United States Patent
Miyaki et al.

(10) Patent No.: US 6,846,890 B2
(45) Date of Patent: Jan. 25, 2005

(54) NORBORNENE DERIVATIVE AND NORBORNENE POLYMER OBTAINED THEREFROM THROUGH RING OPENING POLYMERIZATION

(75) Inventors: Nobuyuki Miyaki, Chiba-ken (JP); Yoshikazu Miyamoto, Chiba-ken (JP); Seiji Fukuhara, Chiba-ken (JP); Toshihiro Ootsuki, Chiba-ken (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 10/488,096

(22) PCT Filed: Oct. 8, 2002

(86) PCT No.: PCT/JP02/10433
§ 371 (c)(1),
(2), (4) Date: Mar. 8, 2004

(87) PCT Pub. No.: WO03/033454
PCT Pub. Date: Apr. 24, 2003

(65) Prior Publication Data
US 2004/0242824 A1 Dec. 2, 2004

(30) Foreign Application Priority Data
Oct. 10, 2001 (JP) ......................... 2001-313178
Feb. 15, 2002 (JP) ......................... 2002-039120
Feb. 26, 2002 (JP) ......................... 2002-049481

(51) Int. Cl.[7] .............................................. C08G 61/06
(52) U.S. Cl. .............................. 526/281; 560/8; 560/9; 560/10; 560/18; 560/19; 560/55; 560/56; 560/64; 560/100; 560/106; 560/107; 556/489
(58) Field of Search .......................... 526/281; 560/8, 560/100, 106, 107, 9, 10, 18, 19, 55, 56, 64; 556/489

(56) References Cited

U.S. PATENT DOCUMENTS

| | | | | |
|---|---|---|---|---|
| 3,489,792 A | * | 1/1970 | Greeenbaum et al. | 560/20 |
| 3,729,503 A | * | 4/1973 | Gribou et al. | 560/140 |
| 4,250,063 A | | 2/1981 | Kotani et al. | |
| 4,487,954 A | * | 12/1984 | Sugimori et al. | 560/107 |
| 6,429,272 B1 | * | 8/2002 | Liu | 526/281 |

FOREIGN PATENT DOCUMENTS

| | | |
|---|---|---|
| DE | 2807494 | 6/1978 |
| EP | 1053986 | 11/2000 |
| GB | 1086021 | 10/1967 |
| JP | 56-164109 | 12/1981 |
| JP | 2001-98031 | 4/2001 |
| WO | 91/00278 | 1/1991 |
| WO | 01/79324 | 10/2001 |

OTHER PUBLICATIONS

U.S. Appl. No. 10/488,096, filed Mar. 8, 2004, inventor Miyaki et al.
U.S. Appl. No. 10/491,433, filed Apr. 12, 2004, inventor Sekiguchi et al.

* cited by examiner

*Primary Examiner*—Fred Teskin
(74) *Attorney, Agent, or Firm*—Oblon, Spivak, McClelland, Maier & Neustadt, P.C.

(57) ABSTRACT

A novel norbornene derivative represented by a general formula (1m) shown below is provided. By conducting a ring opening polymerization of this norbornene derivative, or by performing a subsequent hydrogenation following the ring opening polymerization, a ring opening polymer or a hydrogenated product thereof with an excellent low birefringence can be obtained.

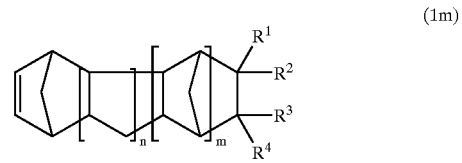

[wherein, at least one of $R^1$ to $R^4$ is a group selected from the group consisting of groups represented by a general formula (1-1) shown below and groups represented by a general formula (1-2) shown below]

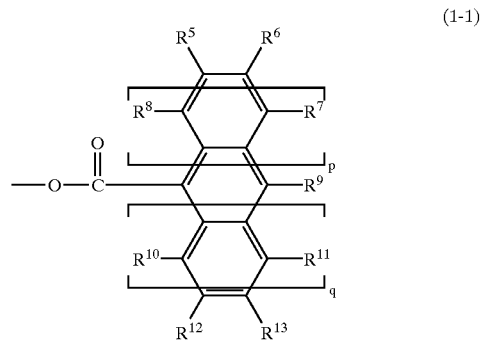

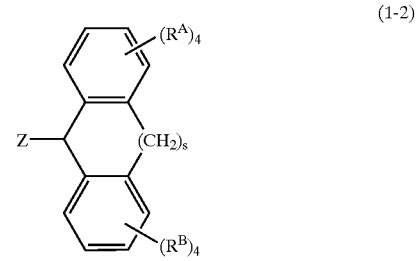

[wherein, at least one of $R^A$, $R^B$ and Z is a group represented by the formula —C(O)O—].

11 Claims, 20 Drawing Sheets

NORBORNENE DERIVATIVE AND NORBORNENE POLYMER OBTAINED THEREFROM THROUGH RING OPENING POLYMERIZATION

TECHNICAL FIELD

The present invention relates to a precursor monomer compound for a cyclic olefin-based polymer which combines excellent transparency and a low birefringence.

In addition, the present invention relates to a norbornene-based ring opening polymer which combines excellent transparency and a low birefringence.

BACKGROUND ART

Conventionally, transparent resins are used as the materials for molded products which typically require transparency such as automobile components, illumination equipment and electrical components. Particularly in recent years, the application of these resins as optical materials, in which the optical properties are important, continues to progress. Examples of known transparent resins which can be ideally applied to such applications include polycarbonate-based resins and acrylic-based resins. However, although acrylic-based resins offer excellent transparency, they have problems in terms of heat resistance and water resistance. In contrast, polycarbonate-based resins offer superior performance to acrylic resins in terms of heat resistance and water resistance, but suffer from different problems such as a high birefringence.

As a result, recently, cyclic polyolefin-based resins which combine transparency, water resistance (low water absorption), a low birefringence, and heat resistance have started to be used as the transparent resins for optical materials.

Polymers synthesized using cyclic olefins as monomers are amorphous due to the presence of bulky alicyclic structures on the principal chain skeleton, display excellent transparency and heat resistance, and moreover also offer other characteristics such as little optical distortion, low water absorption, acid and alkali resistance, and a high level of electrical insulation, and consequently they have been developed for display applications (such as retardation films, diffusion films, liquid crystal substrates, films for touch panels and light guide plates), optical lens applications, optical disk applications (such as CD, MD, CD-R and DVD), optical fiber applications, optical film/sheet applications, optical semiconductor sealing applications, printed wiring board applications (such as rigid printed wiring boards, flexible printed wiring boards and multi layer printed wiring boards), and as substrates for transparent conductive films. Amongst such cyclic olefins, development has centered around cyclic olefin-based polymers with highly reactive norbornenes as precursors.

Cyclic olefin-based polymers such as those described above are typically converted to products by fabrication using molding methods such as injection molding and molten extrusion molding, although with conventional cyclic olefin-based polymers, the birefringence which develops due to the polymer orientation during the molding process has not always satisfied the demanded characteristics, and as a result, the optical characteristics of the generated optical product also failed to meet the demanded characteristics. With the improvements in electronic technology in recent years, the development of a material which retains the excellent transparency and heat resistance characteristics of conventional cyclic olefin-based polymers, but enables a reduction in the birefringence which develops due to the polymer orientation has been keenly sought, although until now, such a material had yet to be discovered.

DISCLOSURE OF INVENTION

A first aspect of the present invention provides a norbornene derivative represented by a general formula (1m) shown below:

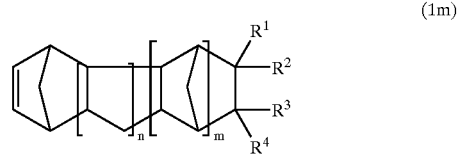

(1m)

[wherein, at least one of $R^1$ to $R^4$ is a group selected from the group consisting of an aromatic ring-containing group represented by a general formula (1-1) shown below and an aromatic ring-containing group represented by a general formula (1-2) shown below, any remaining groups among $R^1$, $R^2$, $R^3$ and $R^4$, where present, represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, and m and n each represent, independently, an integer from 0 to 2];

(1-1)

[wherein, $R^5$ to $R^{13}$ each represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, and p and q each represent, independently an integer from 0 to 2, provided that in a case in which p=q=0, $R^6$ and $R^9$, and/or $R^{13}$ and $R^9$, are bonded to each other to form a carbon homocyclic ring or a heterocyclic ring (this carbon homocyclic ring or heterocyclic ring may be a single ring structure, or may form a polycyclic structure by condensation with at least one other ring), or alternatively at least one of $R^5$, $R^6$, $R^9$, $R^{12}$ and $R^{13}$ is a substituted or unsubstituted aromatic group];

(1-2)

$$\text{Z}-\underset{(R^B)_4}{\overset{(R^A)_4}{\underset{\phantom{X}}{\bigotimes}}}(CH_2)_s$$

[wherein, Z, $R^A$ and $R^B$ each represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, provided that one of $R^A$, $R^B$ and Z is a group represented by a formula —C(O)O— in which the carbonyl group side is bonded to a carbon atom of a ring structure within the formula (1-2), and s represents an integer of 0 or greater].

A second aspect of the present invention provides a norbornene-based ring opening polymer comprising a structural unit represented by a general formula (1) shown below:

(1)

[wherein, X is a group represented by a formula —CH=CH— or a group represented by a formula —CH$_2$CH$_2$—, and m, n, $R^1$, $R^2$, $R^3$ and $R^4$ are as defined above in relation to the general formula (1m)],
wherein the plurality of X groups which exist may be the same or different.

A third aspect of the present invention provides a method of producing a norbornene-based ring opening polymer with a structural unit (1) represented by the general formula (1) shown above (and in which X is a group represented by the formula —CH=CH—), wherein a norbornene-based monomer comprising a norbornene derivative represented by the general formula (1m) shown above is subjected to ring opening polymerization.

In addition, a fourth aspect of the present invention provides a method of producing a norbornene-based ring opening polymer with a structural unit (1) represented by the general formula (1) shown above (and in which X is a group represented by the formula —CH$_2$CH$_2$—), wherein a norbornene-based monomer comprising a norbornene derivative represented by the general formula (1m) shown above is subjected to ring opening polymerization.

BEST MODE FOR CARRYING OUT THE INVENTION

Figure 1:
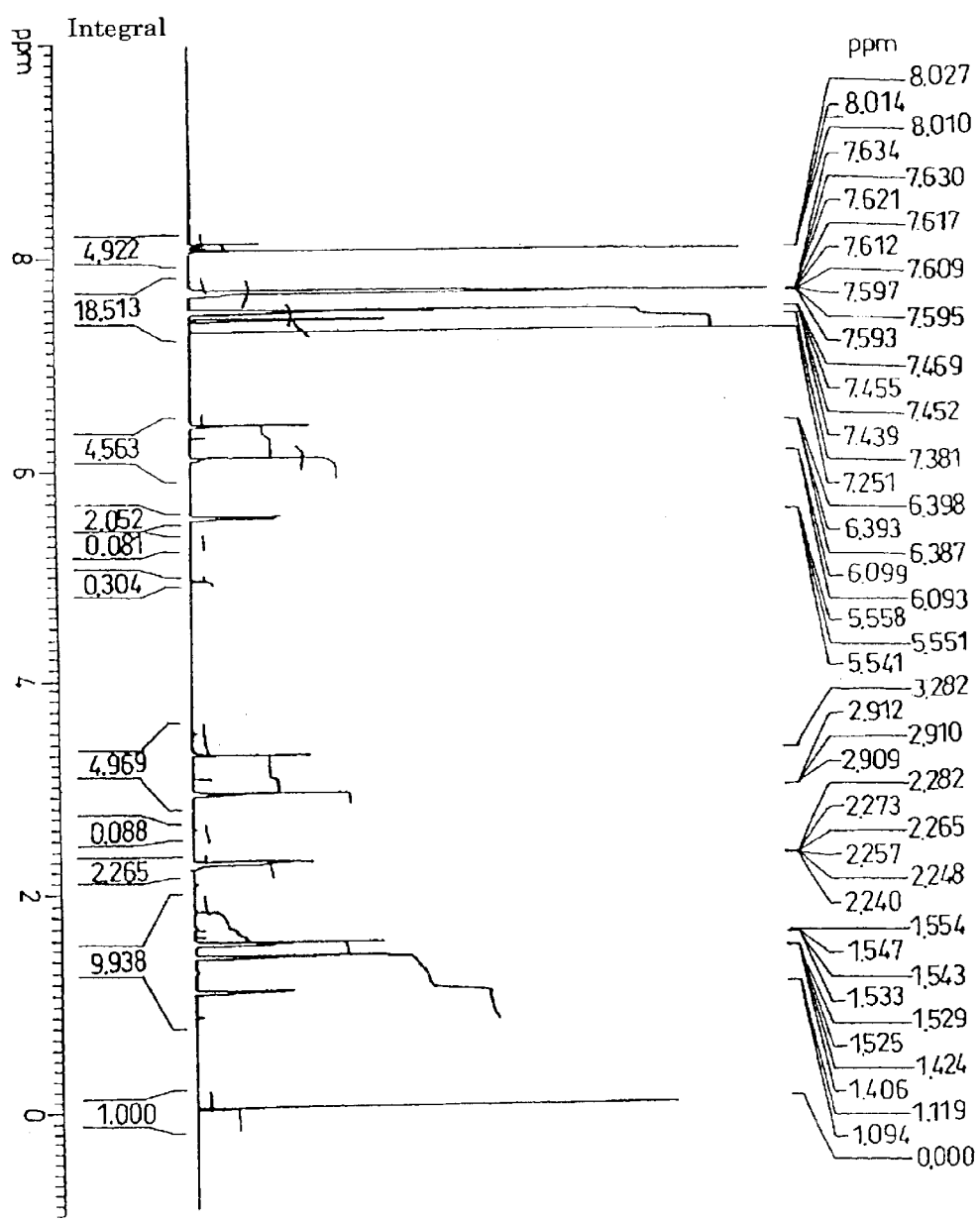
FIG. 1 is a $^1$H-NMR spectrum of 5-(4-biphenylcarbonyloxy)bicyclo[2.2.1]hept-2-ene obtained in an example 1.

As follows is a more detailed description of the present invention.
[Norbornene Derivative]

A norbornene derivative of the present invention is a compound represented by a general formula (1m) shown below.

(1m)

[wherein, at least one of $R^1$ to $R^4$ is a group selected from the group consisting of an aromatic ring-containing group represented by a general formula (1-1) shown below and an aromatic ring-containing group represented by a general formula (1-2) shown below, any remaining groups among $R^1$, $R^2$, $R^3$ and $R^4$, where present, represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, and m and n each represent, independently, an integer from 0 to 2];

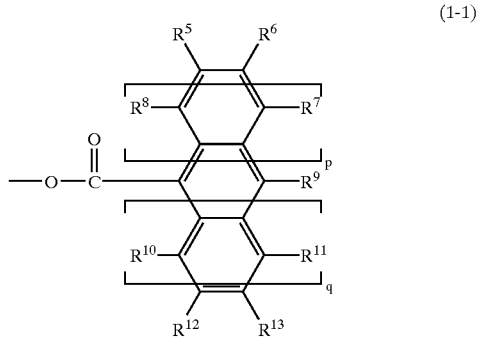

(1-1)

[wherein, $R^5$ to $R^{13}$ each represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, and p and q each represent, independently an integer from 0 to 2, provided that in a case in which p=q=0, $R^6$ and $R^9$, and/or $R^{13}$ and $R^9$, are bonded to each other to form a carbon homocyclic ring or a heterocyclic ring (this carbon homocyclic ring or heterocyclic ring may be a single ring structure, or may form a polycyclic structure by condensation with another ring), or alternatively at least one of $R^5$, $R^6$, $R^9$, $R^{12}$ and $R^{13}$ is a substituted or unsubstituted aromatic group];

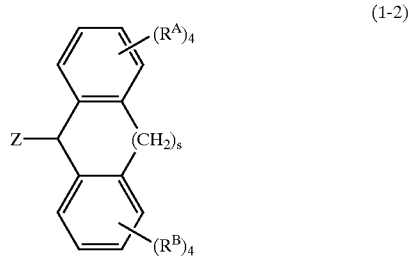

(1-2)

[wherein, Z, $R^A$ and $R^B$ each represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, provided that one of $R^A$, $R^B$ and Z is a group represented by a formula —C(O)O— in which the carbonyl group side is bonded to a carbon atom of a ring structure within the formula (1-2), and s represents an integer of 0, or 1 or greater].

As follows is a description of the groups $R^1$ to $R^{13}$, Z, $R^A$ and $R^B$ from the aforementioned general formula (1m), the general formula (1-1) and the general formula (1-2), each of which represent a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group.

Examples of halogen atoms include fluorine atoms, chlorine atoms and bromine atoms.

Examples of monovalent hydrocarbon groups of 1 to 30 carbon atoms include alkyl groups such as methyl groups, ethyl groups and propyl groups; cycloalkyl groups such as cyclopentyl groups and cyclohexyl groups; alkenyl groups such as vinyl groups and allyl groups; alkylidene groups such as ethylidene groups and propylidene groups; and aromatic groups such as phenyl groups. These hydrocarbon groups may be substituted, and suitable substituent groups include halogen atoms such as fluorine, chlorine and bromine, phenylsulfonyl groups and cyano groups and the like.

Furthermore, the aforementioned substituted or unsubstituted hydrocarbon group may be either bonded directly to the ring structure, or bonded via a linkage group. Examples of suitable linkage groups include bivalent hydrocarbon groups of 1 to 10 carbon atoms (such as alkylene groups represented by —($CH_2$)$_m$— (wherein m is an integer of 1 to 10)); and linkage groups comprising oxygen, nitrogen, sulfur or silicon (such as carbonyl groups (—CO—), carbonyloxy groups (—COO—), oxycarbonyl groups (—OCO—), sulfonyl groups (—$SO_2$—), ether linkages (—O—), thioether linkages (—S—), imino groups (—NH—), amide linkages (—NHCO—), and siloxane linkages (—Si(R)$_2$O— (wherein R represents an alkyl group such as a methyl group or an ethyl group), or linkage groups incorporating a combination of two or more of these linkages.

Examples of monovalent polar groups include hydroxy groups, and alkoxy groups of 1 to 10 carbon atoms, carbonyloxy groups, alkoxycarbonyl groups, aryloxycarbonyl groups, cyano groups, amide groups, imide groups, triorganosiloxy groups, triorganosilyl groups, amino groups, acyl groups, alkoxysilyl groups, sulfonic acid groups and carboxyl groups. Specific examples include alkoxy groups such as methoxy groups and ethoxy groups; carbonyloxy groups including alkylcarbonyloxy groups such as acetoxy groups and propionyloxy groups as well as arylcarbonyloxy groups such as benzoyloxy groups; alkoxycarbonyl groups such as methoxycarbonyl groups and ethoxycarbonyl groups; aryloxycarbonyl groups such as phenoxycarbonyl groups, naphthyloxycarbonyl groups, fluorenyloxycarbonyl groups and biphenylyloxycarbonyl groups; triorganosiloxy groups such as trimethylsiloxy groups and triethylsiloxy groups; triorganosilyl groups such as trimethylsilyl groups and triethylsilyl groups; amino groups such as primary amino groups; and alkoxysilyl groups such as trimethoxysilyl groups and triethoxysilyl groups.

As described above, in the general formula (1-1), in the case in which p=q=0, $R^6$ and $R^9$, and/or $R^{13}$ and $R^9$, are mutually bonded together in pairs and form a carbon homocyclic ring or a heterocyclic ring (this carbon homocyclic ring or heterocyclic ring may be a single ring structure, or may form a polycyclic structure by condensation with another ring. Furthermore, the formed carbon homocyclic ring or heterocyclic ring may be aromatic or non-aromatic), or alternatively at least one of $R^5$, $R^6$, $R^9$, $R^{12}$ and $R^{13}$ is a substituted or unsubstituted aromatic group. Examples of substituent groups on this aromatic group include cyano groups, alkoxy groups, carbonyloxy groups, alkoxycarbonyl groups, amide groups, imide groups, amino groups, acyl groups and halogen atoms.

In the case described above in which p=q=0, if for example $R^6$ and $R^9$ are bonded together and form a benzene ring, and $R^5$, $R^{12}$ and $R^{13}$ are hydrogen atoms, then the group represented by the general formula (1-1) becomes a 2-naphthalenecarbonyloxy group. Examples in which $R^6$ and $R^9$, and/or $R^{13}$ and $R^9$ are mutually bonded together in pairs, forming ring structures, are partially shown below.

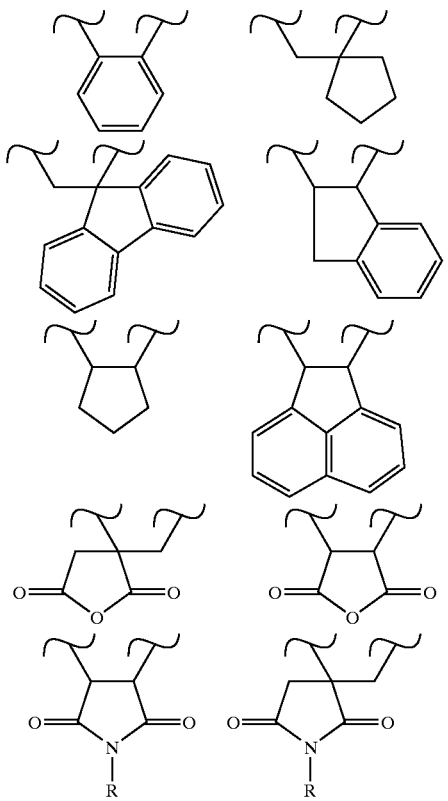

[In the above formulas, R represents a hydrocarbon group of 1 to 20 carbon atoms, including alkyl groups such as methyl groups, ethyl groups and propyl groups, aryl groups such as phenyl groups, and aralkyl groups such as benzyl groups.]

Furthermore, in the aforementioned general formula (1-2), s is either 0 or an integer of 1 or greater, although is preferably from 0 to 2, and even more preferably 0.

In the general formula (1m), in the case in which n=0, and m=0 or 1, the structure must comprise at least 10 mol %, and preferably at least 25 mol %, and even more preferably at least 50 mol %, of stereoisomers in which at least one of the groups selected from the group consisting of substituent groups represented by the general formula (1-1) and the general formula (1-2) is bonded to an α position shown in the partial structural formula represented by a formula (3) shown below. If this proportion is less than 10 mol %, then when the polymer is formed, a reduction in birefringence cannot be expected.

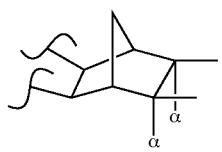
(3)

Furthermore in a similar manner, in the general formula (1m), in the case in which n=0, and m=0 or 1, then for only one of the groups among $R^1$ to $R^4$, the endo form/exo form molar ratio in the stereoisomers of the substituent group represented by the general formula (1-1) or the general formula (1-2) is typically within a range from 10/90 to 100/0, and preferably from 25/75 to 100/0, and even more preferably from 50/50 to 100/0.

As follows is a more specific description of the norbornene derivative represented by the general formula (1m), although the invention is not restricted to the examples presented here.

An example of a norbornene derivative of the present invention is the ester compound produced by the reaction of a norbornene alcohol and an aromatic carboxylic acid, and more specific examples include the compounds shown below.

<Examples in which m=n=0, and $R^1$ to $R^4$=a group represented by the general formula (1-1)>
5-(1-naphthalenecarbonyloxy)-5-methylbicyclo[2.2.1]hept-2-ene
5-(1-naphthalenecarbonyloxy)bicyclo[2.2.1]hept2-ene
5-(2-naphthalenecarbonyloxy)-5-methylbicyclo[2.2.1]hept-2-ene
5-(2-naphthalenecarbonyloxy)bicyclo[2.2.1]hept-2-ene
5-(4-biphenylcarbonyloxy)-5-methylbicyclo[2.2.1]hept-2-ene
5-(4-biphenylcarbonyloxy)bicyclo[2.2.1]hept-2-ene
5-(2-biphenylcarbonyloxy)-5-methylbicyclo[2.2.1]hept-2ene
5-(2-biphenylcarbonyloxy)bicyclo[2.2.1]hept-2-ene
5-(3-biphenylcarbonyloxy)-5-methylbicyclo[2.2.1]hept-2-ene
5-(3-biphenylcarbonyloxy)bicyclo[2.2.1]hept-2ene
5-(9-anthracenecarbonyloxy)-5-methylbicyclo[2.2.1]hept-2-ene
5-(9-anthracenecarbonyloxy)bicyclo[2.2.1]hept-2-ene
5-(2-naphthalenecarbonyloxy)-6-chlorobicyclo[2.2.1]hept-2-ene
5-(4-biphenylcarbonyloxy)-6-chlorobicyclo[2.2.1]hept-2-ene
5-(2-naphthalenecarbonyloxy)-6-methylbicyclo[2.2.1]hept-2-ene
5-(4-biphenylcarbonyloxy)-6-methylbicyclo[2.2.1]hept-2-ene
5-(2-naphthalenecarbonyloxy)-6-phenylbicyclo[2.2.1]hept-2-ene
5-(4-biphenylcarbonyloxy)-6-phenylbicyclo[2.2.1]hept-2-ene
5-(2-naphthalenecarbonyloxy)-6-phenoxycarbonylbicyclo[2.2.1]hept-2-ene
5-(4-biphenylcarbonyloxy)-6-phenoxycarbonylbicyclo[2.2.1]hept-2-ene <Examples in which m=n=0, and $R^1$ to $R^4$=a group represented by the general formula (1-2)>
5-(9-fluorenecarbonyloxy)-5-methylbicyclo[2.2.1]hept-2-ene
5-(9-fluorenecarbonyloxy)bicyclo[2.2.1]hept-2-ene
5-(2-fluorenecarbonyloxy)-5-methylbicyclo[2.2.1]hept-2-ene
5-(2-fluorenecarbonyloxy)bicyclo[2.2.1]hept-2-ene
5-(3-fluorenecarbonyloxy)bicyclo[2.2.1]hept-2-ene
5-(4-fluorenecarbonyloxy)bicyclo[2.2.1]hept-2-ene
5-[1-(9,10-dihydroanthracene)carbonyloxy]bicyclo[2.2.1]hept-2-ene
5-[2-(9,10-dihydroanthracene)carbonyloxy]bicyclo[2.2.1]hept-2-ene
5-[9-(9,10-dihydroanthracene)carbonyloxy]bicyclo[2.2.1]hept-2-ene <Examples in which m=1, n=0, and $R^1$ to $R^4$=a group represented by the general formula (1-1)>
8-(1-naphthalenecarbonyloxy)-8-methyltetracyclo[4.4.0.1$^{2,5}$.1$^{7,10}$]-3-dodecene 8-(1-naphthalenecarbonyloxy)tetracyclo[4.4.0.1$^{2,5}$.1$^{7,10}$]-3-dodecene 8-(2-naphthalenecarbonyloxy)-8-methyltetracyclo[4.4.0.1$^{2,5}$.1$^{7,10}$]-3-dodecene 8-(2-naphthalenecarbonyloxy)tetracyclo[4.4.0.1$^{2,5}$.1$^{7,10}$]-3-dodecene 8-(4-biphenylcarbonyloxy)-8-methyltetracyclo[4.4.0.1$^{2,5}$.1$^{7,10}$]-3-dodecene 8-(4-biphenylcarbonyloxy)tetracyclo[4.4.0.1$^{2,5}$.1$^{7,10}$]-3-dodecene 8-(3-biphenylcarbonyloxy)-8-methyltetracyclo[4.4.0.1$^{2,5}$.1$^{7,10}$]-3-dodecene 8-(3-biphenylcarbonyloxy)tetracyclo[4.4.0.1$^{2,5}$.1$^{7,10}$]-3-dodecene 8-(2-biphenylcarbonyloxy)-8-methyltetracyclo[4.4.0.1$^{2,5}$.1$^{7,10}$]-3-dodecene 8-(2-biphenylcarbonyloxy)tetracyclo[4.4.0.1$^{2,5}$.1$^{7,10}$]-3-dodecene 8-(9-anthracenecarbonyloxy)-8-methyltetracyclo[4.4.0.1$^{2,5}$.1$^{7,10}$]-3-dodecene 8-(9-anthracenecarbonyloxy)tetracyclo[4.4.0.1$^{2,5}$.1$^{7,10}$]-3-dodecene 8-(2naphthalenecarbonyloxy)-9-chlorotetracyclo[4.4.0.1$^{2,5}$.1$^{7,10}$]-3-dodecene 8-(4-biphenylcarbonyloxy)-9-chlorotetracyclo[4.4.0.1$^{2,5}$.1$^{7,10}$]-3-dodecene 8-(2-naphthalenecarbonyloxy)-9-methyltetracyclo[4.4.0.1$^{2,5}$.1$^{7,10}$]-3-dodecene 8-(4-biphenylcarbonyloxy)-9-phenyltetracyclo[4.4.0.1$^{2,5}$.1$^{7,10}$]-3-dodecene 8-(2-naphthalenecarbonyloxy)-9-phenyltetracyclo[4.4.0.1$^{2,5}$.1$^{7,10}$]-3-dodecene 8-(4-biphenylcarbonyloxy)-9-phenyltetracyclo[4.4.0.1$^{2,5}$.1$^{7,10}$]-3-dodecene 8-(2-naphthalenecarbonyloxy)-9-phenoxycarbonyltetracyclo[4.4.0.1$^{2,5}$.1$^{7,10}$]-3-dodecene 8-(4-biphenylcarbonyloxy)-9-phenoxycarbonyltetracyclo[4.4.0.1$^{2,5}$.1$^{7,10}$]-3-dodecene <Examples in which m=1, n=0, and R$^1$ to R$^4$=a group represented by the general formula (1-2)>

8-(9-fluorenecarbonyloxy)-8-methyltetracyclo[4.4.0.1$^{2,5}$.1$^{7,10}$]-3-dodecene 8-(9-fluorenecarbonyloxy)tetracyclo[4.4.0.1$^{2,5}$.1$^{7,10}$]-3-dodecene 8-(2-fluorenecarbonyloxy)-8-methyltetracyclo[4.4.0.1$^{2,5}$.1$^{7,10}$]-3-dodecene 8-(2-fluorenecarbonyloxy)tetracyclo[4.4.0.1$^{2,5}$.1$^{7,10}$]-3-dodecene 8-(3-fluorenecarbonyloxy)tetracyclo[4.4.0.1$^{2,5}$.1$^{7,10}$]-3-dodecene 8-(4-fluorenecarbonyloxy)tetracyclo[4.4.0.1$^{2,5}$.1$^{7,10}$]-3-dodecene 8-[1-(9,10-dihydroanthracene)carbonyloxy]tetracyclo[4.4.0.1$^{2,5}$.1$^{7,10}$]-3-dodecene 8-[2-(9,10-dihydroanthracene)carbonyloxy]tetracyclo[4.4.0.1$^{2,5}$.1$^{7,10}$]-3-dodecene 8-[9-(9,10-dihydroanthracene)carbonyloxy]tetracyclo[4.4.0.1$^{2,5}$.1$^{7,10}$]-3-dodecene <Examples in which m=n=1, and R$^1$ to R$^4$=a group represented by the general formula (1-1)>

12-(1-naphthalenecarbonyloxy)pentacyclo[9.2.1.1$^{4,7}$.0$^{2,10}$.0$^{3,8}$]-5-pentadecene 12-(2-naphthalenecarbonyloxy)pentacyclo[9.2.1.1$^{4,7}$.0$^{2,10}$.0$^{3,8}$]-5-pentadecene 12-(4-biphenylcarbonyloxy)pentacyclo[9.2.1.1$^{4,7}$.0$^{2,10}$.0$^{3,8}$]-5-pentadecene 12-(2-biphenylcarbonyloxy)pentacyclo[9.2.1.1$^{4,7}$.0$^{2,10}$.0$^{3,8}$]-5-pentadecene 12-(3-biphenylcarbonyloxy)pentacyclo[9.2.1.1$^{4,7}$.0$^{2,10}$.0$^{3,8}$]-5-pentadecene 12-(9-anthracenecarbonyloxy)pentacyclo[9.2.1.1$^{4,7}$.0$^{2,10}$.0$^{3,8}$]-5-pentadecene <Examples in which m=n=1, and R$^1$ to R$^4$=a group represented by the general formula (1-2)>

12-(9-fluorenecarbonyloxy)pentacyclo[9.2.1.1$^{4,7}$.0$^{2,10}$.0$^{3,8}$]-5-pentadecene 12-(2-fluorenecarbonyloxy)pentacyclo[9.2.1.1$^{4,7}$.0$^{2,10}$.0$^{3,8}$]-5-pentadecene 12-[9-(9,10-dihydroanthracene)carbonyloxy]pentacyclo[9.2.1.1$^{4,7}$.0$^{2,10}$.0$^{3,8}$]-5-pentadecene Of these, norbornene derivatives wherein in the general formula (1m), m=1 and n=0, and three of R$^1$ to R$^4$ are hydrogen atoms and the remaining one group of R$^1$ to R$^4$ is a group represented by either the general formula (1-1) or the general formula (1-2) produce polymers with high heat deformation resistance and low water absorption and are consequently preferred. In addition, use of either 5-(2-naphthalenecarbonyloxy)bicyclo[2.2.1]hept-2-ene or 5-(4-biphenylcarbonyloxy)bicyclo[2.2.1]hept-2-ene produces a polymer that is effective in producing molded products with excellent low birefringence.

A norbornene derivative of the present invention can be converted to a desired polymer by a ring opening polymerization, a ring opening polymerization followed by a hydrogenation reaction, an addition polymerization, a radical polymerization, a cationic polymerization or an anionic polymerization or the like. Furthermore, where necessary, copolymers can also be produced by copolymerization with an arbitrary copolymerizable compound. Polymers synthesized from a norbornene derivative of the present invention display excellent transparency, low water absorption and a low birefringence.

[Norbornene-based Ring Opening Polymer]

A norbornene-based ring opening polymer of the present invention comprises a structural unit (1) represented by a general formula (1) shown below as an essential structural unit, although in some cases, the polymer may also comprise a structural unit (2) represented by a general formula (2) shown below.

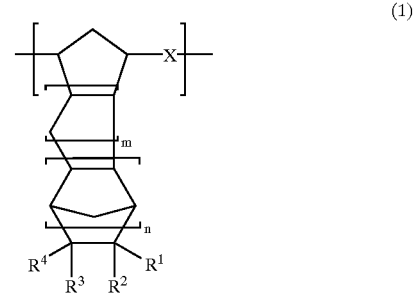

(1)

[wherein, X is a group represented by a formula —CH=CH— or a group represented by a formula —CH$_2$CH$_2$—, and m, n, R$^1$, R$^2$, R$^3$ and R$^4$ are as defined above in relation to the general formula (1m) of the aforementioned norbornene derivative.]

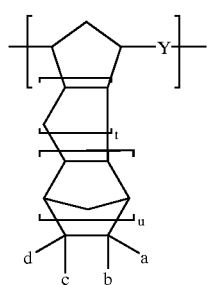

(2)

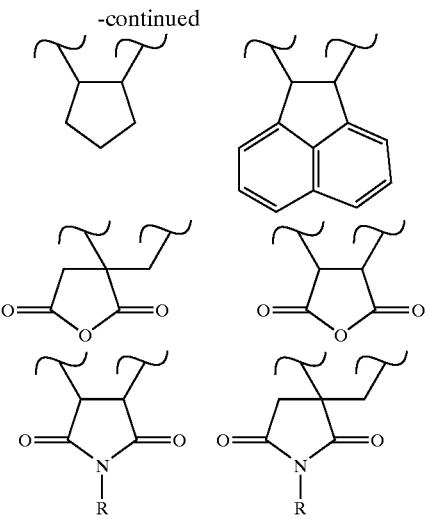
-continued

[wherein, t and u each represent, independently, an integer from 0 to 2, Y is a group represented by a formula —CH=CH— or a group represented by a formula —CH$_2$CH$_2$—, a, b, c and d each represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, or alternatively a and b, b and c, or c and d may be bonded to each other to form a carbon homocyclic ring or a heterocyclic ring (this carbon homocyclic ring or heterocyclic ring may be a single ring structure, or may form a polycyclic structure by condensation with another ring).]

The groups $R^1$ to $R^4$ in the general formula (1) are the same as the groups $R^1$ to $R^4$ in the general formula (1m) of the norbornene derivative described above.

In the general formula (2), the hydrogen atom; halogen atom; substituted or unsubstituted monovalent hydrocarbon group of 1 to 30 carbon atoms which may contain a linkage group containing oxygen, nitrogen, sulfur or silicon; or monovalent polar group represented by a to d, are the same as the examples given for the halogen atom; substituted or unsubstituted monovalent hydrocarbon group of 1 to 30 carbon atoms which may contain a linkage group containing oxygen, nitrogen, sulfur or silicon; or monovalent polar group represented by $R^1$ to $R^4$ in the general formula (1m) relating to the aforementioned norbornene derivative.

Furthermore, in the general formula (2), a and b, b and c, and c and d may be mutually bonded in pairs and form a carbon homocyclic ring or a heterocyclic ring (this carbon homocyclic ring or heterocyclic ring may be a single ring structure, or may form a polycyclic structure by condensation with another ring). Each carbon homocyclic ring or heterocyclic ring thus formed may be either an aromatic ring or a non-aromatic ring. Examples in which a ring structure is formed are partially shown below.

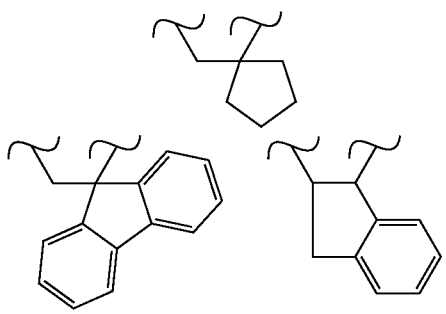

[In the above formulas, R represents a hydrocarbon group of 1 to 20 carbon atoms, including alkyl groups such as methyl groups, ethyl groups and propyl groups, aryl groups such as phenyl groups, and aralkyl groups such as benzyl groups.]

In those cases in which a norbornene-based ring opening polymer comprises a structural unit (1) and a structural unit (2), the proportion of the structural unit (2) relative to the combined total of the structural unit (1) and the structural unit (2) is preferably no more than 95% by weight. More specifically, the ratio of structural unit (1)/structural unit (2), expressed as a weight ratio, is typically within a range from 100/0 to 5/95, and preferably from 100/0 to 30/70, and even more preferably from 100/0 to 50/50.

A norbornene-based ring opening polymer of the present invention may also incorporate other structural units in addition to the structural unit (1) and the structural unit (2). These structural units are described in the production methods below in terms of raw material monomers that can be used arbitrarily.

-Production Methods-

A norbornene-based ring opening polymer of the present invention can be produced by a ring opening polymerization of a norbornene-based monomer (hereafter termed the "monomer (1)") represented by a general formula (1m) shown below, sometimes together with a norbornene-based monomer (hereafter termed the "monomer (2)") represented by a general formula (2m) shown below.

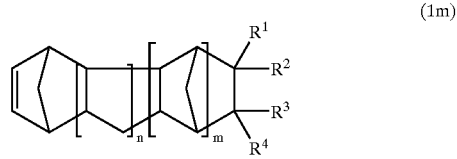

(1m)

[wherein, m, n, $R^1$, $R^2$, $R^3$ and $R^4$ are as defined above in relation to the general formula (1m) of the aforementioned norbornene derivative.]

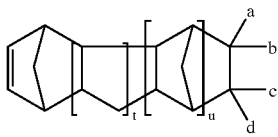

(2m)

[wherein, t, u, a, b, c and d are as defined above in relation to the general formula (2).]

The quantities of the monomers used during this polymerization, expressed as a weight ratio of the monomer (1) and the monomer (2) is typically within a range from 100/0 to 5/95, and preferably from 100/0 to 30/70, and even more preferably from 100/0 to 50/50.

The ring opening polymerization described above enables the production of a norbornene-based ring opening polymer of the present invention containing the structural unit (1), and in those cases in which the monomer (2) is used, also containing the structural unit (2). In this case, both the X group in the structural unit (1) and the Y group in the structural unit (2) are unsaturated groups represented by the formula —CH=CH—.

If a norbornene-based ring opening polymer obtained in this manner is subsequently hydrogenated, then the aforementioned ethylene-based unsaturated group is hydrogenated, and the aforementioned X and Y groups are converted to a group represented by the formula —CH$_2$—CH$_2$—.

As follows is a more specific description of the monomer (1) and (2), although the invention is not restricted to the examples presented here.

Examples of the monomer (1) used in the present invention include, for example, ester compounds produced by the reaction of a norbornene alcohol and an aromatic carboxylic acid, and more specifically, the compounds listed above in relation to the aforementioned norbornene derivative. The compounds listed can be used either singularly, or in combinations of two or more compounds.

Of the compounds, norbornene-based monomers wherein in the general formula (1m), m=1 and n=0, and three of $R^1$ to $R^4$ are hydrogen atoms and the remaining one group of $R^1$ to $R^4$ is a group represented by either the general formula (1-1) or the general formula (1-2) described in relation to the general formula (1m) of the aforementioned norbornene derivative produce polymers with high heat resistance and low water absorption and are consequently preferred. In addition, use of either 5-(2-naphthalenecarbonyloxy)bicyclo[2.2.1]hept-2-ene or 5-(4-biphenylcarbonyloxy)bicyclo[2.2.1]hept-2-ene is effective in producing molded products with low birefringence.

Specific examples of the structural unit (2) used in the present invention include the following:
bicyclo[2.2.1]hept-2-ene,
tricyclo[5.2.1.0$^{2,6}$]-8-decene,
tetracyclo[4.4.0.1$^{2,5}$.1$^{7,10}$]-3-dodecene,
pentacyclo[6.5.1.1$^{3,6}$.0$^{2,7}$.0$^{9,13}$]-4-pentadecene,
pentacyclo[9.2.1.1$^{4,7}$.0$^{2,10}$.0$^{3,8}$]-5-pentadecene,
tricyclo[4.4.0.1$^{2,5}$]-3-undecene,
5-methylbicyclo[2.2.1]hept-2-ene,
5-ethylbicyclo[2.2.1]hept-2-ene,
5-methoxycarbonylbicyclo[2.2.1]hept-2-ene,
5-methyl-5-methoxycarbonylbicyclo[2.2.1]hept-2-ene,
5-cyanobicyclo[2.2.1]hept-2-ene,
8-methoxycarbonyltetracyclo[4.4.0.1$^{2,5}$.1$^{7,10}$]-3-dodecene,
8-ethoxycarbonyltetracyclo[4.4.0.1$^{2,5}$.1$^{7,10}$]-3-dodecene,
8-n-propoxycarbonyltetracyclo[4.4.0.1$^{2,5}$.1$^{7,10}$]-3-dodecene,
8-isopropoxycarbonyltetracyclo[4.4.0.1$^{2,5}$.1$^{7,10}$]-3-dodecene,
8-n-butoxycarbonyltetracyclo[4.4.0.1$^{2,5}$.1$^{7,10}$]-3-dodecene,
8-phenoxycarbonyltetracyclo[4.4.0.1$^{2,5}$.1$^{7,10}$]-3-dodecene,
8-(1-naphthoxy)carbonyltetracyclo[4.4.0.1$^{2,5}$.1$^{7,10}$]-3-dodecene,
8-(2-naphthoxy)carbonyltetracyclo[4.4.0.1$^{2,5}$.1$^{7,10}$]-3-dodecene,
8-(4-phenylphenoxy)carbonyltetracyclo[4.4.0.1$^{2,5}$.1$^{7,10}$]-3-dodecene,
8-methyl-8-methoxycarbonyltetracyclo[4.4.0.1$^{2,5}$.1$^{7,10}$]-3-dodecene,
8-methyl-8-ethoxycarbonyltetracyclo[4.4.0.1$^{2,5}$.1$^{7,10}$]-3-dodecene,
8-methyl-8-n-propoxycarbonyltetracyclo[4.4.0.1$^{2,5}$.1$^{7,10}$]-3-dodecene,
8-methyl-8-isopropoxycarbonyltetracyclo[4.4.0.1$^{2,5}$.1$^{7,10}$]-3-dodecene,
8-methyl-8-n-butoxycarbonyltetracyclo[4.4.0.1$^{2,5}$.1$^{7,10}$]-3-dodecene,
8-8-methyl-8-phenoxycarbonyltetracyclo[4.4.0.1$^{2,5}$.1$^{7,10}$]-3-dodecene,
8-methyl-8-(1-naphthoxy)carbonyltetracyclo[4.4.0.1$^{2,5}$.1$^{7,10}$]-3-dodecene,
8-methyl-8-(2-naphthoxy)carbonyltetracyclo[4.4.0.1$^{2,5}$.1$^{7,10}$]-3-dodecene,
8-methyl-8-(4-phenylphenoxy)carbonyltetracyclo[4.4.0.1$^{2,5}$.1$^{7,10}$]-3-dodecene,
pentacyclo[9.2.1.1$^{4,7}$.0$^{2,10}$.0$^{3,8}$]-5-pentadecene,
heptacyclo[13.2.1.1$^{3,13}$.1$^{6,9}$.0$^{2,14}$.0$^{4,12}$.0$^{5,10}$]-7-eicosene,
heptacyclo[8.8.0.1$^{4,7}$.1$^{11,18}$.1$^{13,16}$.0$^{3,8}$.0$^{12,17}$]-5-heneicosene,
5-ethylidenebicyclo[2.2.1]hept-2-ene,
8-ethylidenetetracyclo[4.4.0.1$^{2,5}$.1$^{7,10}$]-3dodecene,
5-phenylbicyclo[2.2.1]hept-2-ene,
8-phenyltetracyclo[4.4.0.1$^{2,5}$.1$^{7,10}$]-3-dodecene,
5-ethylbicyclo[2.2.1]hept-2-ene,
5-n-butylbicyclo[2.2.1]hept-2-ene,
5-n-hexylbicyclo[2.2.1]hept-2-ene,
5-cyclohexylbicyclo[2.2.1]hept-2-ene,
5-n-octylbicyclo[2.2.1]hept-2-ene,
5-n-decylbicyclo[2.2.1]hept-2-ene,
5-isopropylbicyclo[2.2.1]hept-2-ene,
5-phenylbicyclo[2.2.1]hept-2-ene,
5-(1-naphthyl)bicyclo[2.2.1]hept-2-ene,
5-(2-naphthyl)bicyclo[2.2.1]hept-2-ene,
5-(2-naphthyl)-5-methylbicyclo[2.2.1]hept-2-ene,
5-(4-biphenyl)bicyclo[2.2.1]hept-2-ene,
5-(4biphenyl)-5-methylbicyclo[2.2.1]hept-2-ene,
5-aminomethylbicyclo[2.2.1]hept-2-ene,
5-trimethoxysilylbicyclo[2.2.1]hept-2-ene,
5-triethoxysilylbicyclo[2.2.1]hept-2-ene,
5-tripropoxysilylbicyclo[2.2.1]hept-2-ene,
5-tributoxysilylbicyclo[2.2.1]hept-2-ene,
5-chloromethylbicyclo[2.2.1]hept-2-ene,
5-hydroxymethylbicyclo[2.2.1]hept-2-ene,
5-(3-cyclohexenyl)bicyclo[2.2.1]hept-2-ene,
5-fluorobicyclo[2.2.1]hept-2-ene,
5-fluoromethylbicyclo[2.2.1]hept-2-ene,
5-trifluoromethylbicyclo[2.2.1]hept-2-ene,
5-pentafluoroethylbicyclo[2.2.1]hept-2-ene,
5,5-difluorobicyclo[2.2.1]hept-2-ene,
5,6-difluorobicyclo[2.2.1]hept-2-ene, 5,5-bis(trifluoromethyl)bicyclo[2.2.1]hept-2-ene,
5,6-bis(trifluoromethyl)bicyclo[2.2.1]hept-2-ene,
5-methyl-5-trifluoromethylbicyclo[2.2.1]hept-2-ene,
5,5,6-trifluorobicyclo[2.2.1]hept-2-ene,
5,5,6-tris(trifluoromethyl)bicyclo[2.2.1]hept-2-ene,
5,5,6,6-tetrafluorobicyclo[2.2.1]hept-2-ene,
5,5,6,6-tetrakis(trifluoromethyl)bicyclo[2.2.1]hept-2-ene,
5,5-difluoro-6,6-bis(trifluoromethyl)bicyclo[2.2.1]hept-2-ene,
5,6-difluoro-5,6-bis(trifluoromethyl)bicyclo[2.2.1]hept-2-ene,
5,5,6-trifluoro-6-trifluoromethylbicyclo[2.2.1]hept-2-ene,
5-fluoro-5-pentafluoroethyl-6,6-bis(trifluoromethyl)bicyclo[2.2.1]hept-2-ene,
5,6-difluoro-5-pentafluoro-iso-propyl-6-trifluoromethyl-bicyclo[2.2.1]hept-2-ene,
5-chloro-5,6,6-trifluorobicyclo[2.2.1]hept-2-ene,
5,6-dichloro-5,6-bis(trifluoromethyl)bicyclo[2.2.1]hept-2-ene,
5,5,6-trifluoro-6-trifluoromethoxybicyclo[2.2.1]hept-2-ene,
5,5,6-trifluoro-6-heptafluoropropoxybicyclo[2.2.1]hept-2-ene,
8-fluorotetracyclo[4.4.0.1$^{2,5}$.1$^{7,10}$]-3-dodecene,
8-fluoromethyltetracyclo[4.4.0.1$^{2,5}$.1$^{7,10}$]-3-dodecene,
8-difluoromethyltetracyclo[4.4.0.1$^{2,5}$.1$^{7,10}$]-3-dodecene,
8-trifluoromethyltetracyclo[4.4.0.1$^{2,5}$.1$^{7,10}$]-3-dodecene,
8-pentafluoroethyltetracyclo[4.4.0.1$^{2,5}$.1$^{7,10}$]-3-dodecene,
8,8-difluorotetracyclo[4.4.0.1$^{2,5}$.1$^{7,10}$]-3-dodecene,
8,9-difluorotetracyclo[4.4.0.1$^{2,5}$.1$^{7,10}$]-3-dodecene,
8,8-bis(trifluoromethyl)tetracyclo[4.4.0.1$^{2,5}$.1$^{7,10}$]-3-dodecene,
8,9-bis(trifluoromethyl)tetracyclo[4.4.0.1$^{2,5}$.1$^{7,10}$]-3-dodecene,
8-methyl-8-trifluoromethyltetracyclo[4.4.0.1$^{2,5}$.1$^{7,10}$]-3-dodecene,
8,8,9-trifluorotetracyclo[4.4.0.1$^{2,5}$.1$^{7,10}$]-3-dodecene,
8,8,9-tris(trifluoromethyl)tetracyclo[4.4.0.1$^{2,5}$.1$^{7,10}$]-3-dodecene,
8,8,9,9-tetrafluorotetracyclo[4.4.0.1$^{2,5}$.1$^{7,10}$]-3-dodecene,
8,8,9,9-tetrakis(trifluoromethyl)tetracyclo[4.4.0.1$^{2,5}$.1$^{7,10}$]-3-dodecene,
8,8-difluoro-9,9-bis(trifluoromethyl)tetracyclo[4.4.0.1$^{2,5}$.1$^{7,10}$]-3-dodecene,
8,9-difluoro-8,9-bis(trifluoromethyl)tetracyclo[4.4.0.1$^{2,5}$.1$^{7,10}$]-3-dodecene,
8,8,9-trifluoro-9-trifluoromethyltetracyclo[4.4.0.1$^{2,5}$.1$^{7,10}$]-3-dodecene,
8,8,9-trifluoro-9-trifluoromethoxytetracyclo[4.4.0.1$^{2,5}$.1$^{7,10}$]-3-dodecene,
8,8,9-trifluoro-9-pentafluoropropoxytetracyclo[4.4.0.1$^{2,5}$.1$^{7,10}$]-3-dodecene,
8-fluoro-8-pentafluoroethyl-9,9-bis(trifluoromethyl)tetracyclo[4.4.0.1$^{2,5}$.1$^{7,10}$]-3-dodecene,
8,9-difluoro-8-heptafluoroiso-propyl-9-trifluoromethyl-tetracyclo[4.4.0.1$^{2,5}$.1$^{7,10}$]-3-dodecene,
8-chloro-8,9,9-trifluorotetracyclo[4.4.0.1$^{2,5}$.1$^{7,10}$]-3-dodecene,
8,9-dichloro-8,9-bis(trifluoromethyl)tetracyclo[4.4.0.1$^{2,5}$.1$^{7,10}$]-3-dodecene,
8-(2,2,2-trifluoroethoxycarbonyl)tetracyclo[4.4.0.1$^{2,5}$.1$^{7,10}$]-3-dodecene, and
8-methyl-8-(2,2,2-trifluoroethoxycarbonyl)tetracyclo[4.4.0.1$^{2,5}$.1$^{7,10}$]-3-dodecene.

These norbornene-based monomers may be used in combination with the monomer (1), either singularly or in combinations of two or more compounds.

Of these monomers, from the viewpoint of achieving a copolymer with a balance between heat resistance, water absorption, and adhesion and bonding with other materials, norbornene-based monomers in which at least one of a to d in the general formula (2m) is a carboxylate ester residue represented by —$(CH_2)_kCOOR^{22}$ (wherein, $R^{22}$ is a hydrocarbon group of 1 to 20 carbon atoms, and k is an integer from 0 to 10) are preferred. In addition, 8-methyl-8-methoxycarbonyltetracyclo[4.4.0.1$^{2,5}$.1$^{7,10}$]-3-dodecene is particularly preferred as the production method is simple.

Examples of the hydrocarbon group of 1 to 20 carbon atoms represented by the aforementioned $R^{22}$ include alkyl groups such as methyl groups, ethyl groups and propyl groups, aryl groups such as phenyl groups, and aralkyl groups such as benzyl groups. Methyl groups, ethyl groups and phenyl groups are preferred, and methyl groups are particularly desirable.

In a production method of the present invention, examples of copolymerizable monomers which can be used other than the monomer (1) and the monomer (2) include cycloolefins such as cyclobutene, cyclopentene, cyclooctene, and cyclodecene, as well as non-conjugated cyclic polyolenes such as 1,5-cylooctadiene and cyclododecatriene.

In the present production method, the aforementioned ring opening polymerization may also be conducted in the presence of polybutadiene, polyisoprene, styrene-butadiene, ethylene-non-conjugated diene polymers and unhydrogenated ring opening (co)polymers of other norbornene-based monomers.

As follows is a further description of the polymerization conditions.

Ring Opening Polymerization Catalyst:

A ring opening polymerization catalyst used in the present invention utilizes a metathesis catalyst of the type described below. This metathesis catalyst is a combination of (a) at least one compound selected from the group consisting of W, Mo and Re compounds, and (b) at least one compound selected from compounds of a group IA element (such as Li, Na or K), a group IIA element (such as Mg or Ca), a group IIB element (such as Zn, Cd or Hg), a group IIIB element (such as B or Al), a group IVA element (such as Ti or Zr) or a group IVB element (such as Si, Sn or Pb) of the Deming periodic table, which contain at least one bond between the aforementioned element and carbon, or between the aforementioned element and hydrogen.

In order to raise the activity of the catalyst, an additive (c) described below may also be added.

Representative examples of the W, Mo and Re compound of the constituent (a) include those compounds disclosed in Japanese Laid-open publication (kokai) No. 1-240517 (JP1-240517A) such as $WCl_6$, $MoCl_5$ and $ReOCl_3$.

Specific examples of the constituent (b) include those compounds disclosed in Japanese Laid-open publication (kokai) No. 1-240517 (JP1-240517A) such as n-$C_4H_9Li$, $(C_2H_5)_3Al$, $(C_2H_5)_2AlCl$, $(C_2H_5)_{1.5}AlCl_{1.5}$, $(C_2H_5)AlCl_2$, methyl alumoxane and LiH Representative examples of the constituent (c) include alcohols, aldehydes, ketones and amines, as well as those compounds disclosed in Japanese Laid-open publication (kokai) No. 1-240517 (JP1-240517A).

The amount of the metathesis catalyst used should typically result in a molar ratio between the aforementioned constituent (a) and the specified monomers (that is, the monomer (1) and the monomer (2)), namely the ratio of constituent (a):specified monomers, within a range from 1:500 to 1:50,000, and preferably within a range from 1:1000 to 1:10,000. The relative proportions of the constituent (a) and the constituent (b) should produce a metal atom ratio (a):(b) within a range from 1:1 to 1:50, and preferably from 1:2 to 1:30. The relative proportions of the constituent (a) and the constituent (c) should produce a molar ratio (c):(a) within a range from 0.005:1 to 15:1, and preferably from 0.05:1 to 7:1.

Molecular Weight Regulating Agent:

Regulation of the molecular weight of the ring opening polymer can also be achieved through controlling the polymerization temperature, the type of catalyst and the type of solvent, although in the present invention the molecular weight is preferably regulated by adding a molecular weight regulating agent to the reaction system. Examples of suitable molecular weight regulating agents include α-olefins such as ethylene, propene, 1-butene, 1-pentene, 1-hexene, 1-heptene, 1-octene, 1-nonene and 1-decene, as well as styrene, and of these, 1-butene and 1-hexene are particularly preferred. This molecular weight regulating agent may utilize a single compound, or a mixture of two or more different regulating agents. The amount of the molecular weight regulating agent used should be from 0.005 to 0.6 mols per 1 mol of the specified monomer (1) supplied to the ring opening polymerization reaction, with quantities from 0.02 to 0.5 mols being preferred.

Ring Opening Polymerization Reaction Solvent

Examples of suitable solvents for use in the ring opening polymerization reaction (the solvent for dissolving the specified monomers, the metathesis catalyst and the molecular weight regulating agent) include alkanes such as pentane, hexane, heptane, octane, nonane and decane; cycloalkanes such as cyclohexane, cycloheptane, cyclooctane, decalin and norbornane; aromatic hydrocarbons such as benzene, toluene, xylene, ethylbenzene and cumene; halogenated hydrocarbon compounds such as chlorobutane, bromohexane, methylene chloride, dichloroethane, hexamethylene dibromide, chlorobenzene, chloroform and tetrachloroethylene; saturated carboxylate esters such as ethyl acetate, n-butyl acetate, iso-butyl acetate and methyl propionate; and ethers such as dibutyl ether, tetrahydrofuran and dimethoxyethane, and these solvents may be used singularly, or in combinations of two or more solvents. Of the above solvents, the aromatic hydrocarbons are preferred. The amount of solvent used should typically result in a solvent:specified monomers ratio (weight ratio) within a range from 1:1 to 10:1, with ratios from 1:1 to 5:1 being preferred.

Hydrogenation Catalyst

A ring opening polymer obtained in the above manner can be used, as is, although from the viewpoint of heat resistance stability, the use of a hydrogenated polymer, which has undergone hydrogenation, is preferred. What is described as a hydrogenated product or hydrogenated polymer in the present invention refers to compounds in which the olefin-based unsaturated bonds within the principal chain of the polymer produced by the ring opening polymerization of either the monomer (1), or the monomer (1) and the monomer (2), have been hydrogenated, and the side chain aromatic rings based on the monomer (1) or the monomer (2) have undergone essentially no hydrogenation.

The hydrogenation reaction must be performed under conditions wherein the side chain aromatic rings based on the monomer (1) or the monomer (2) undergo essentially no hydrogenation. Typically, a hydrogenation catalyst is added to the ring opening polymer solution, and reaction is then conducted with hydrogen gas at a pressure within a range from normal pressure to 300 atmospheres, and preferably from 3 to 200 atmospheres, and at a temperature within a range from 0 to 200° C., and preferably from 20 to 180° C.

Examples of the hydrogenation catalyst include those catalysts typically used in hydrogenation reactions of olefin-based compounds. These known hydrogenation catalysts include both heterogeneous catalysts and homogeneous catalysts. Examples of suitable heterogeneous catalysts include solid catalysts comprising a noble metal catalytic material such as palladium, platinum, nickel, rhodium or ruthenium supported by a carrier such as carbon, silica, alumina or titania. Examples of suitable homogeneous catalysts include nickel naphthenate/triethyl aluminum, nickel acetylacetonate/triethyl aluminum, cobalt octenate/n-butyl lithium, titanocene dichloride/diethyl aluminum monochloride, rhodium acetate, chlorotris (triphenylphosphine)rhodium, dichlorotris (triphenylphosphine)ruthenium, chlorohydrocarbonyltris (triphenylphosphine)ruthenium, and dichlorocarbonyltris (triphenylphosphine)ruthenium. The catalysts may be in powdered or granulated form. The quantity of the hydrogenation catalyst added must be regulated to ensure that the side chain aromatic rings based on the monomer (1) undergo essentially no hydrogenation, although typically a quantity is used which produces a ring opening polymer:hydrogenation catalyst ratio (weight ratio) within a range from $1:1\times 10^{-6}$ to 1:2.

In a hydrogenated product of a ring opening polymer produced in the present invention, at least 99.0% of the olefin-based unsaturated bonds within the principal chain of the polymer produced by the ring opening polymerization are preferably hydrogenated, whereas the side chain aromatic rings remain essentially unhydrogenated.

The intrinsic viscosity ($\eta_{inh}$) of a ring opening polymer of the present invention or a hydrogenated product thereof, measured using an Ubbelohde viscometer, is typically within a range from 0.25 to 5.0, and preferably from 0.3 to 4.0, and even more preferably from 0.35 to 2.0. Furthermore, in molecular weight measurements using gel permeation chromatography (GPC, tetrahydrofuran solution, polystyrene equivalence), the number average molecular weight (Mn) is typically within a range from 1000 to 500,000, and preferably from 2000 to 300,000, and even more preferably from 3000 to 100,000, and the weight average molecular weight (Mw) is typically within a range from 5000 to 2,000,000, and preferably from 10,000 to 1,000,000, and even more preferably from 30,000 to 500,000. If $\eta_{inh}$ is less than 0.2, Mn is less than 1000, or Mw is less than 5000, then the strength of the molded product deteriorates markedly. In contrast, if $\eta_{inh}$ is greater than 0.5, Mn is greater than 500,000, or Mw is greater than 2,000,000, then the melt viscosity or the solution viscosity of the ring opening polymer or the hydrogenated product thereof becomes overly high, and obtaining the desired molded product may be difficult.

A variety of known additives can be added to a ring opening polymer of the present invention or a hydrogenated product thereof. Examples of such additives include phenol-based or hydroquinone-based antioxidants such as 2,6-di-t-butyl-4-methylphenol, 2,2-methylenebis(4-ethyl-6-t-butylphenol), 2,5-di-t-butylhydroquinone, tetrakis [methylene-3-(3,5-di-t-butyl-4-hydroxyphenyl)propionate] methane, 4,4-thiobis-(6-t-butyl-3methylphenol), 1,4-bis(4-hydroxyphenyl)cyclohexane and octadecyl-3-(3,5-di-t-butyl4-hydroxyphenyl)propionate, as well as phosphorus-based antioxidants such as tris(4-methoxy-3,5-diphenyl) phosphite, tris(nonylphenyl)phosphite and tris(2,4-di-t-butylphenyl)phosphite, and by adding either one, or two or more of these antioxidants, the oxidation stability of the ring opening polymer or the hydrogenated product thereof can be improved. In addition, by adding ultraviolet absorbing agents such as 2,4-dihydroxybenzophenone, 2-hydroxy-4-methoxybenzophenone and 2,2-methylenebis[4-(1,1,3,3-tetramethylbutyl)-6-[(2H-benzotriazol-2-yl)phenol]], the light resistance can be improved. Additives such as lubricants may also be added to improve the workability.

A norbornene-based polymer of the present invention displays excellent transparency, low water absorption and a low birefringence, and moreover generates a uniform retardation. As a result, a polymer of the present invention is useful within fields such as optics, and electrical and electronic materials. For example, the polymers can be ideally applied to use as molding materials for optical disks, magneto-optical disks, optical lenses (such as Fθ lenses, pickup lenses, laser printer lenses and camera lenses), spectacle lenses, optical films or sheets (such as display films, retardation films, polarizing films, polarizing plate protective films, diffusion films, antireflective films, liquid crystal substrates, EL substrates, electronic paper substrates, touch panel substrates and PDP front plates), transparent conductive film substrates, optical fibers, light guide plates, light diffusion plates, optical cards, optical mirrors, IC, LSI and LED sealing materials.

EXAMPLES

As follows is a more detailed description of the present invention using a series of examples. However, the present invention is in no way limited to the examples presented below.

The various measurements and evaluations within the examples and the comparative examples were conducted in the manner described below.

[Monomer Purity]

Monomer purity was determined using a high performance liquid chromatography (HPLC) device manufactured by Tosoh Corporation, and using methanol as the solvent.

[Weight Average Molecular Weight and Molecular Weight Distribution]

The polystyrene equivalent weight average molecular weight (Mw), and the molecular weight distribution (Mw/Mn) were measured using an HLC-8020 gel permeation chromatography (GPC) device manufactured by Tosoh Corporation, and using tetrahydrofuran (THF) as the solvent. Mn represents the number average molecular weight.

[Glass Transition Temperature: Tg]

Using a differential scanning calorimeter (DSC) manufactured by Seiko Instruments Inc., the glass transition temperature was measured under a nitrogen atmosphere, with a rate of temperature increase of 20° C. per minute.

[Measurement of Retardation]

A polymer obtained by polymerization was pelletized, and an optical disk substrate of external diameter 130 mm and internal diameter 15 mm was then formed by injection molding under conditions including a resin temperature of 270° C. and a die temperature of 110° C. using an injection molding device (DISK-3, manufactured by Sumitomo Heavy Industries, Ltd.). Using the thus formed optical disk substrate, the retardation of the 130 mm diameter optical disk substrate, within a range from a radius of 30 to 60 mm from the center of the substrate, was measured by a double pulse method (perpendicular incidence) with a light source wavelength of 633 nm, using a birefringence automatic measurement apparatus (manufactured by Nippon Densi Kogaku co., ltd.), and this retardation value was used as the value for birefringence evaluation. As this retardation value decreases, the molded material can be considered as displaying a lower birefringence.

Example 1

Synthesis of 5-(4-biphenylcarbonyloxy)bicyclo[2.2.1]hept-2-ene

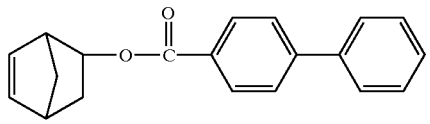

28 g (253.9 mmol) of norbornene alcohol (endo form/exo form molar ratio of 8/1) was measured into a 500 mL flask equipped with a dropping funnel, and the air in the system was replace with nitrogen. 41 mL (507.8 mmol) of pyridine was then added dropwise, and stirred well with a stirrer to dissolve the pyridine. Subsequently, with the temperature of the reaction system maintained at 4±2° C. using an ice bath, and with adequate stirring, 50 g (230.8 mmol) of 4-phenylbenzoyl chloride dissolved in 200 mL of THF (tetrahydrofuran) was gradually added dropwise. Following completion of this dropwise addition, stirring was continued for 1 hour with the reaction system still in the ice bath, and then for a further 1 hour at room temperature, and finally the reaction system was refluxed for 30 minutes. Following cooling to room temperature, the generated pyridine salts were removed by filtration, and the reaction mixture was thoroughly washed with distilled water. The solvent was then removed under reduced pressure, with heating, and the thus obtained crystals were repeatedly recrystallized from n-hexane, yielding 63 g of white crystals of 5-(4-biphenylcarbonyloxy)bicyclo[2.2.1]hept-2-ene (monomer). Analysis of the product crystals by HPLC revealed a purity of 98%.

Figure 2:
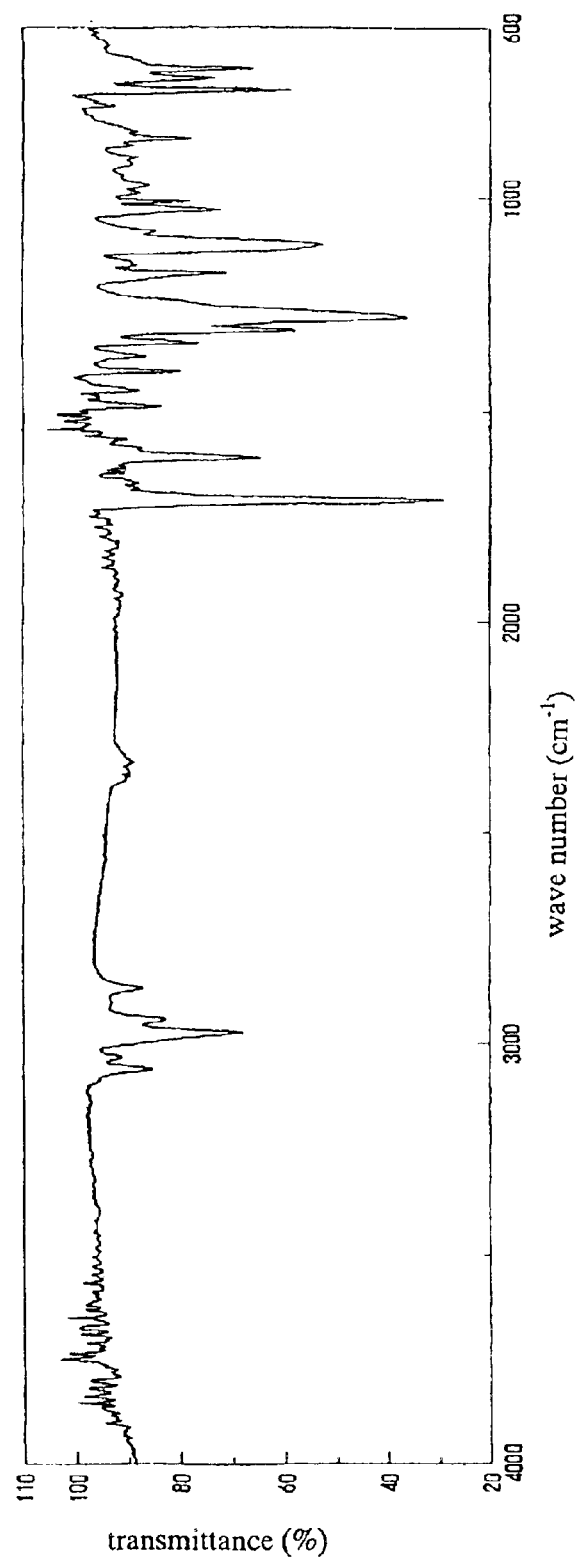
FIG. 2 is an infrared absorption (IR) spectrum of 5-(4-biphenylcarbonyloxy) bicyclo[2.2.1]hept-2-ene obtained in the example 1.

The $^1$H-NMR spectrum and the infrared absorption (IR) spectrum of the product monomer are shown in FIG. 1 and FIG. 2.

In the $^1$H-NMR spectrum shown in FIG. 1, the endo type proton bonded to the carbon at position 5 of the bicyclo[2.2.1]hept-2-ene structure was observed at 4.9 ppm, and the exo type proton was observed at 5.5 ppm, and from the relative intensities, the stereoisomeric ratio (the endo type/exo type molar ratio) for the 4-biphenylcarbonyloxy group within the compound was identified as 8/1. In addition, the protons bonded to the carbons at positions 2 and 3 of the bicyclo[2.2.1]hept-2-ene structure were observed at 6.1 ppm and 6.4 ppm respectively, and the protons bonded to the biphenyl rings were observed within a range from 7.3 to 8.0 ppm, enabling the above compound to be identified.

In the infrared absorption (IR) spectrum shown in FIG. 2, the stretching vibration absorption for the CH groups of the benzene rings was observed within the vicinity of 3055 cm$^{-1}$, and the stretching vibration absorption for the CO group within the ester carbonyl group was observed within the vicinity of 1710 cm$^{-1}$.

Example 2

Synthesis of 5-(2-naphthalenecarbonyloxy)bicyclo[2.2.1]hept-2-ene

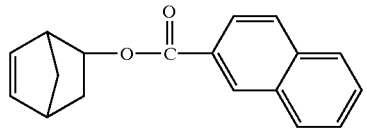

With the exceptions of using 44 g (230.8 mmol) of 2-naphthoyl chloride instead of 4-phenylbenzoyl chloride, and purifying the reactants using a column (filler: Al²O₃, developing solvent: hexane), reaction in the same manner as the example 1 yielded 46 g of a white solid of 5-(2-naphthalenecarbonyloxy)bicyclo[2.2.1]hept-2-ene. Analysis of the product monomer by HPLC revealed a purity of 99%.

Analysis of the ¹H-NMR spectrum in the same manner as described above for the example 1 revealed a stereoisomeric ratio (the endo type/exo type molar ratio) for the substituent group within the monomer of 8/1. Furthermore, in the infrared absorption (IR) spectrum, the stretching vibration absorption for the CH groups of the aromatic rings was observed within the vicinity of 3050 cm⁻¹, and the stretching vibration absorption for the CO group within the ester carbonyl group was observed within the vicinity of 1710 to 1730 cm⁻¹.

Figure 3:
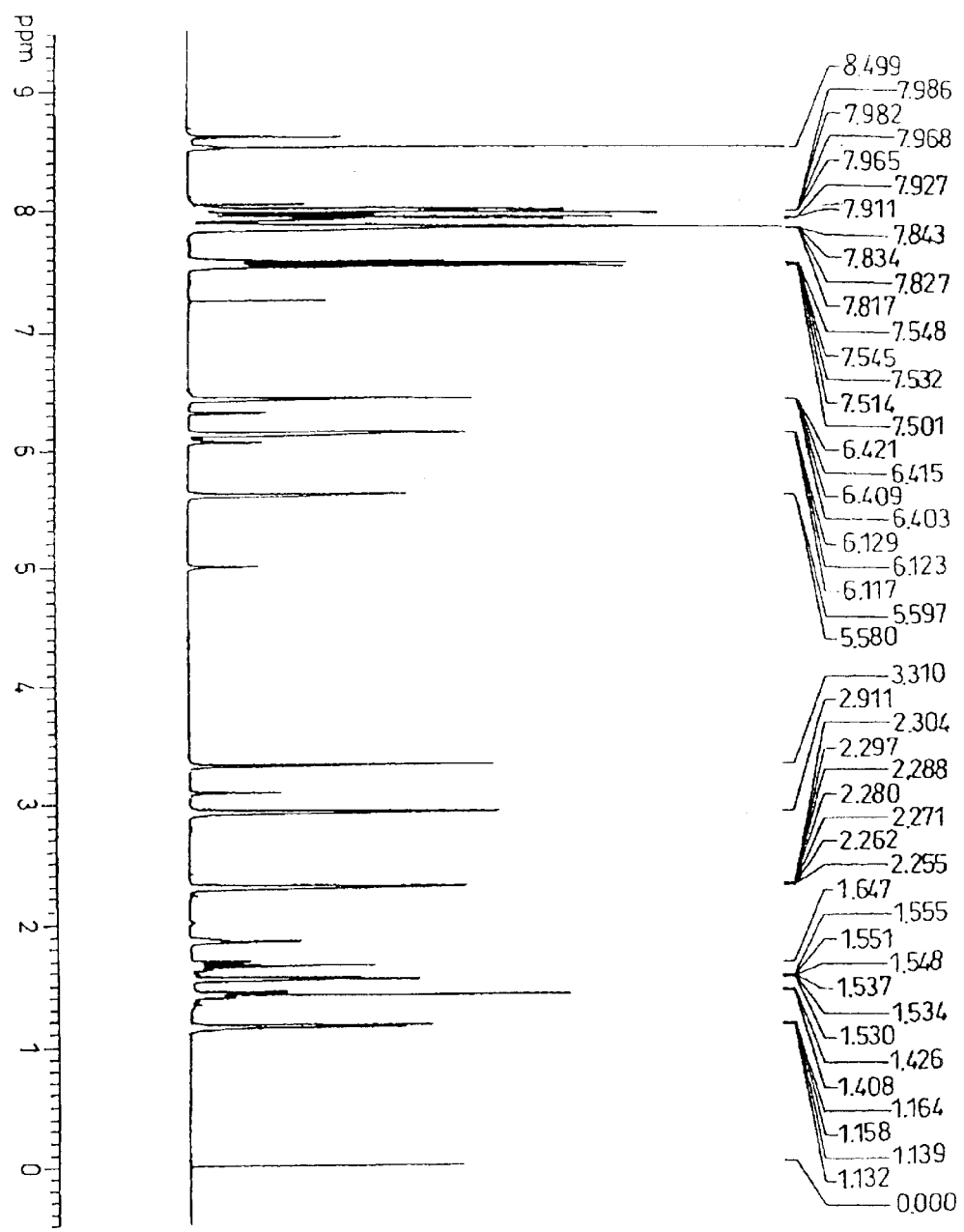
FIG. 3 is a $^1$H-NMR spectrum of 5-(2-naphthalenecarbonyloxy)bicyclo[2.2.1]hept-2-ene obtained in an example 2.
Figure 4:
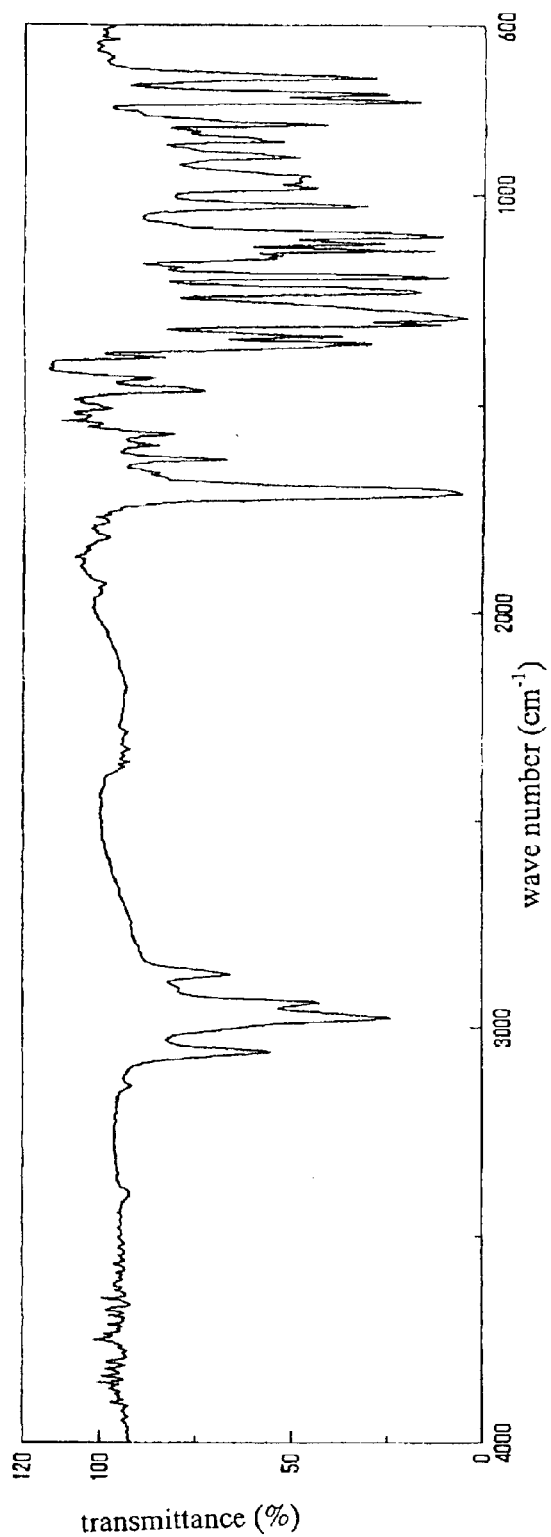
FIG. 4 is an infrared absorption (IR) spectrum of 5-(2-naphthalenecarbonyloxy)bicyclo[2.2.1]hept-2-ene obtained in the example 2.

The ¹H-NMR spectrum and the infrared absorption (IR) spectrum of the product monomer are shown in FIG. 3 and FIG. 4.

Example 3

Synthesis of 5-(1-naphthalenecarbonyloxy)bicyclo[2.2.1]hept-2-ene

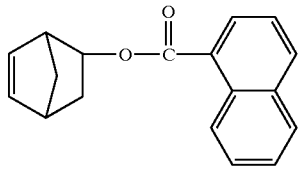

With the exception of using 44 g (230.8 mmol) of 1-naphthoyl chloride instead of 2-naphthoyl chloride, reaction in the same manner as the example 2 yielded 43.8 g of a transparent liquid of 5-(1-naphthalenecarbonyloxy)bicyclo[2.2.1]hept-2-ene. Analysis of the product monomer by HPLC revealed a purity of 98%.

Analysis of the ¹H-NMR spectrum in the same manner as described above for the example 1 revealed a stereoisomeric ratio (the endo type/exo type molar ratio) for the substituent group within the monomer of 8/1. Furthermore, in the infrared absorption (IR) spectrum, the stretching vibration absorption for the CH groups of the aromatic rings was observed within the vicinity of 3050 cm⁻¹, and the stretching vibration absorption for the CO group within the ester carbonyl group was observed within the vicinity of 1710 to 1730 cm⁻¹.

Figure 5:
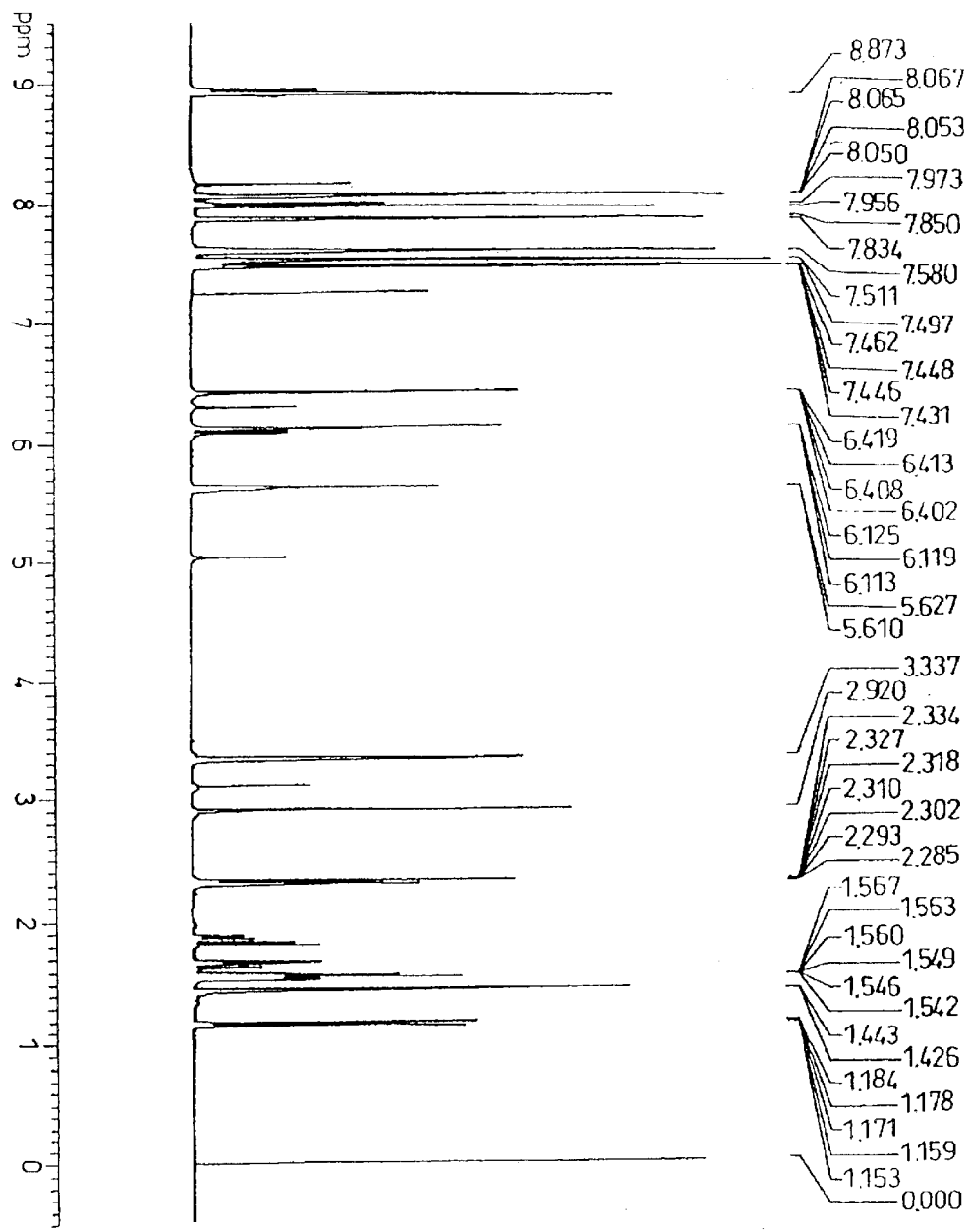
FIG. 5 is a $^1$H-NMR spectrum of 5-(1-naphthalenecarbonyloxy)bicyclo[2.2.1]hept-2-ene obtained in an example 3.
Figure 6:
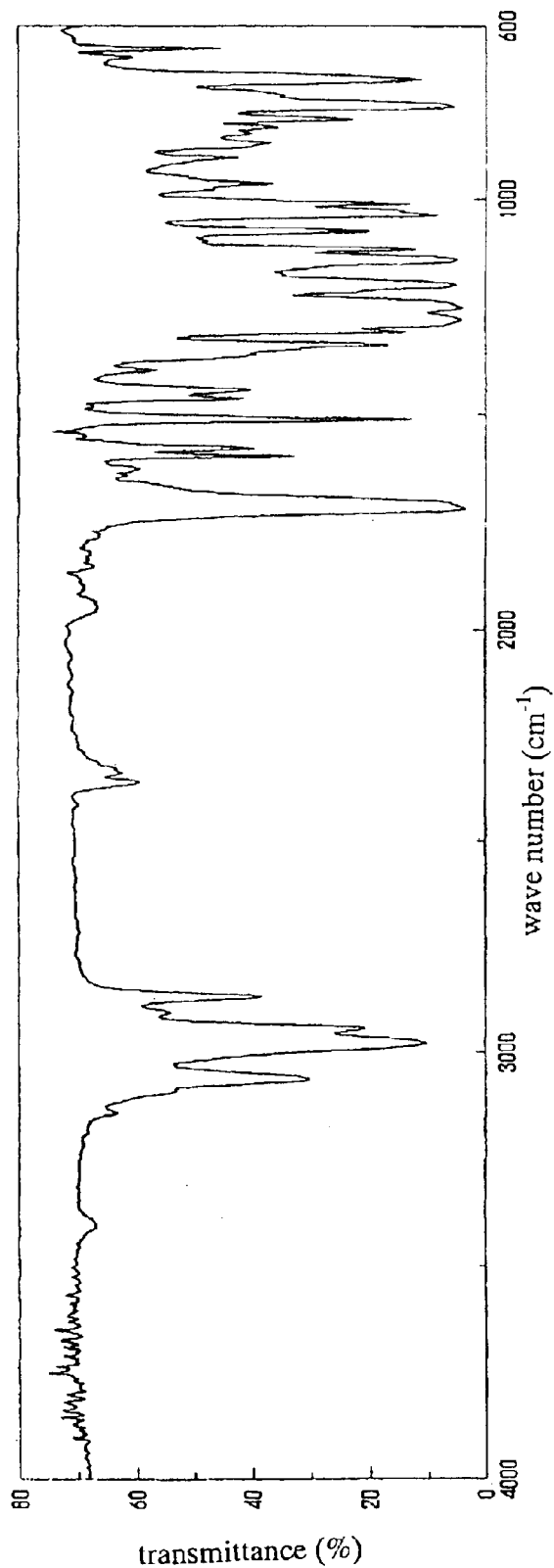
FIG. 6 is an infrared absorption (IR) spectrum of 5-(1-naphthalenecarbonyloxy)bicyclo[2.2.1]hept-2-ene obtained in the example 3.

The ¹H-NMR spectrum and the infrared absorption (IR) spectrum of the product monomer are shown in FIG. 5 and FIG. 6.

Example 4

Synthesis of 5-(9-anthracenecarbonyloxy)bicyclo[2.2.1]hept-2-ene

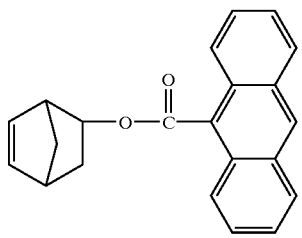

With the exceptions of using 55.5 g (230.8 mmol) of 9-anthracenoyl chloride instead of 4-phenylbenzoyl chloride, purifying the reactants using a column (filler: Al₂O₃, developing solvent: hexane), and performing recrystallization using a hexane/methylene chloride mixed solvent, reaction in the same manner as the example 1(1) yielded 25.9 g of a light yellow colored solid of 5-(9-anthracenecarbonyloxy)bicyclo[2.2.1]hept-2-ene. Analysis of the product monomer by HPLC revealed a purity of 98%.

Analysis of the ¹H-NMR spectrum in the same manner as described above for the example 1 revealed a stereoisomeric ratio (the endo type/exo type molar ratio) for the substituent group within the monomer of 8/1. Furthermore, in the infrared absorption (IR) spectrum, the stretching vibration absorption for the CH groups of the aromatic rings was observed within the vicinity of 3050 cm⁻¹, and the stretching vibration absorption for the CO group within the ester carbonyl group was observed within the vicinity of 1710 to 1730 cm⁻¹.

Figure 7:
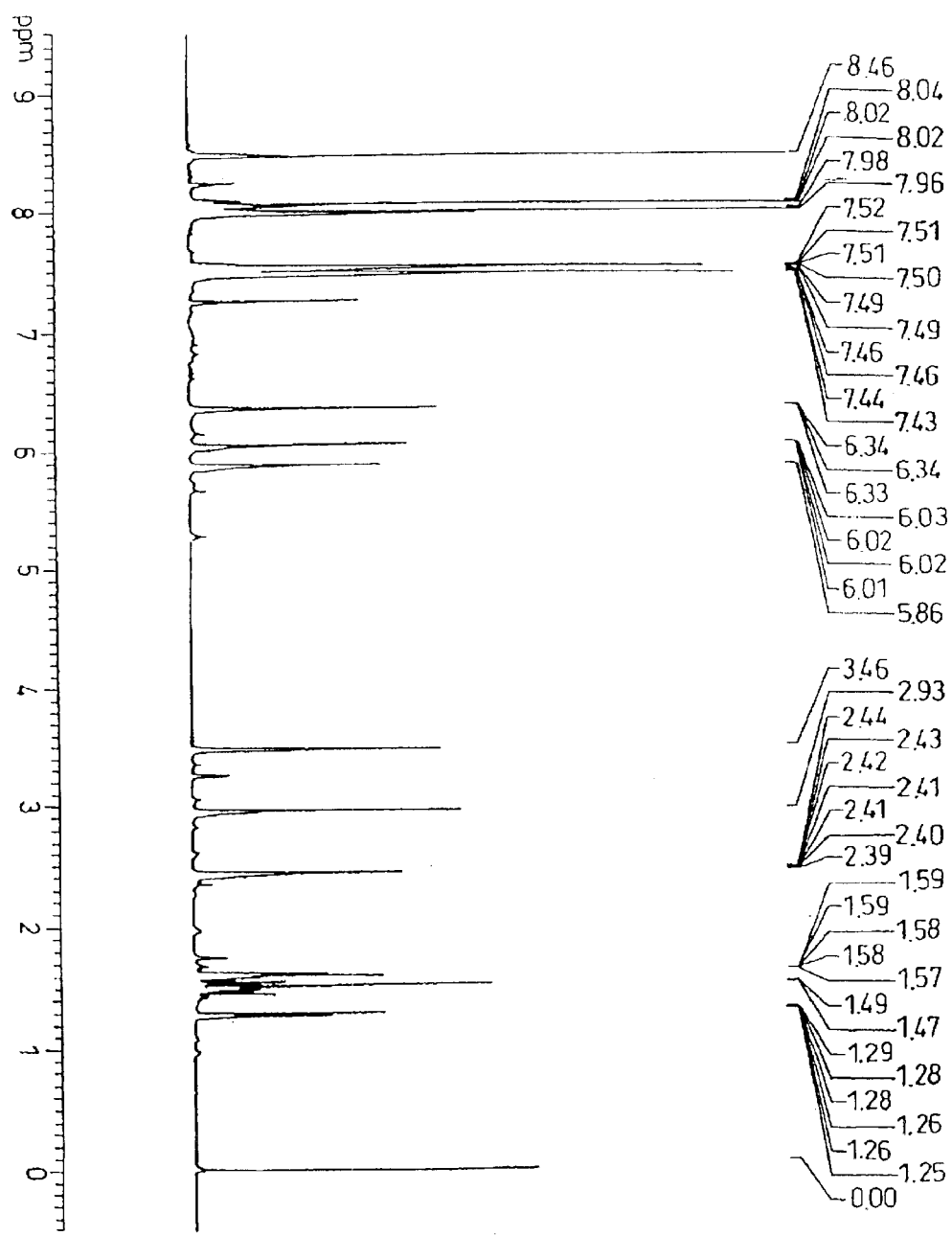
FIG. 7 is a $^1$H-NMR spectrum of 5-(9-anthracenecarbonyloxy)bicyclo[2.2.1]hept-2-ene obtained in an example 4.
Figure 8:
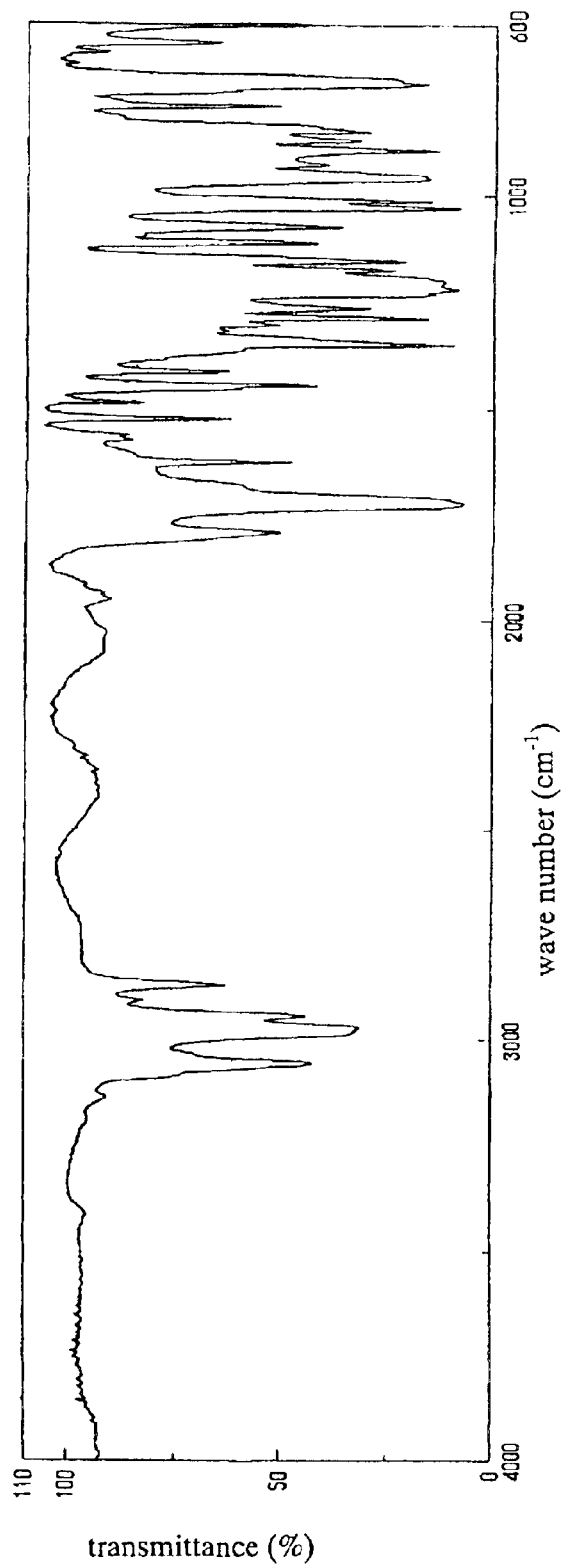
FIG. 8 is an infrared absorption (IR) spectrum of 5-(9-anthracenecarbonyloxy)bicyclo[2.2.1]hept-2-ene obtained in the example 4.

The ¹H-NMR spectrum and the infrared absorption (IR) spectrum of the product monomer are shown in FIG. 7 and FIG. 8.

Example 5

Synthesis of 5-(9-fluorenecarbonyloxy)bicyclo[2.2.1]hept-2-ene

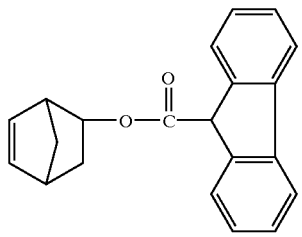

With the exception of using 52.8 g (230.8 mmol) of 9-fluorenoyl chloride instead of 9-anthracenoyl chloride, reaction in the same manner as the example 4 yielded 14.0 g of a yellow colored solid of 5-(9-fluorenecarbonyloxy)bicyclo[2.2.1]hept-2-ene. Analysis of the product monomer by HPLC revealed a purity of 98%.

Analysis of the ¹H-NMR spectrum in the same manner as described above for the example 1 revealed a stereoisomeric ratio (the endo type/exo type molar ratio) for the substituent group within the monomer of 8/1. Furthermore, in the infrared absorption (IR) spectrum, the stretching vibration absorption for the CH groups of the aromatic rings was observed within the vicinity of 3050 cm⁻¹, and the stretching vibration absorption for the CO group within the ester carbonyl group was observed within the vicinity of 1710 to 1730 cm⁻¹.

Figure 9:
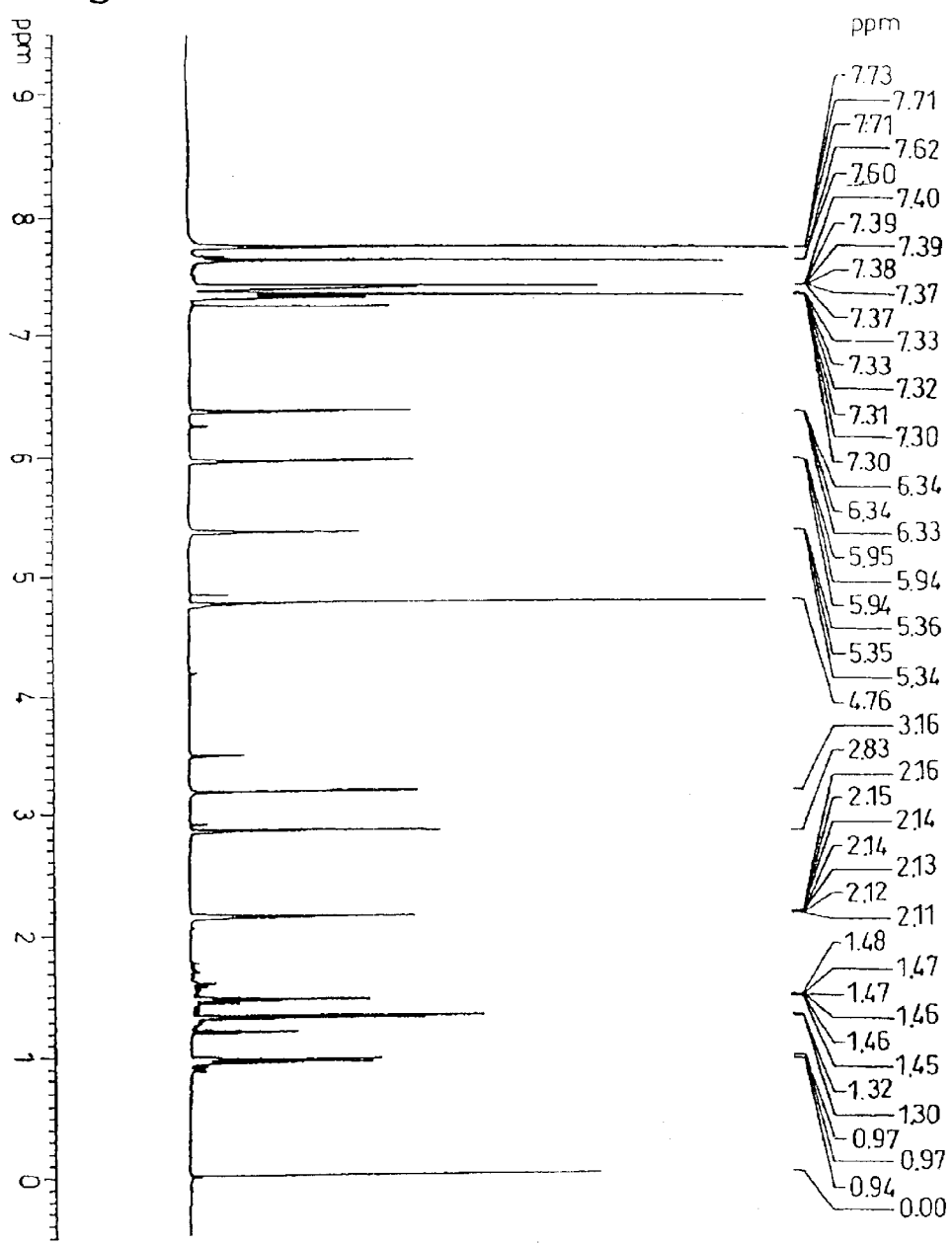
FIG. 9 is a $^1$H-NMR spectrum of 5-(9-fluorenecarbonyloxy)bicyclo[2.2.1]hept-2-ene obtained in an example 5.
Figure 10:
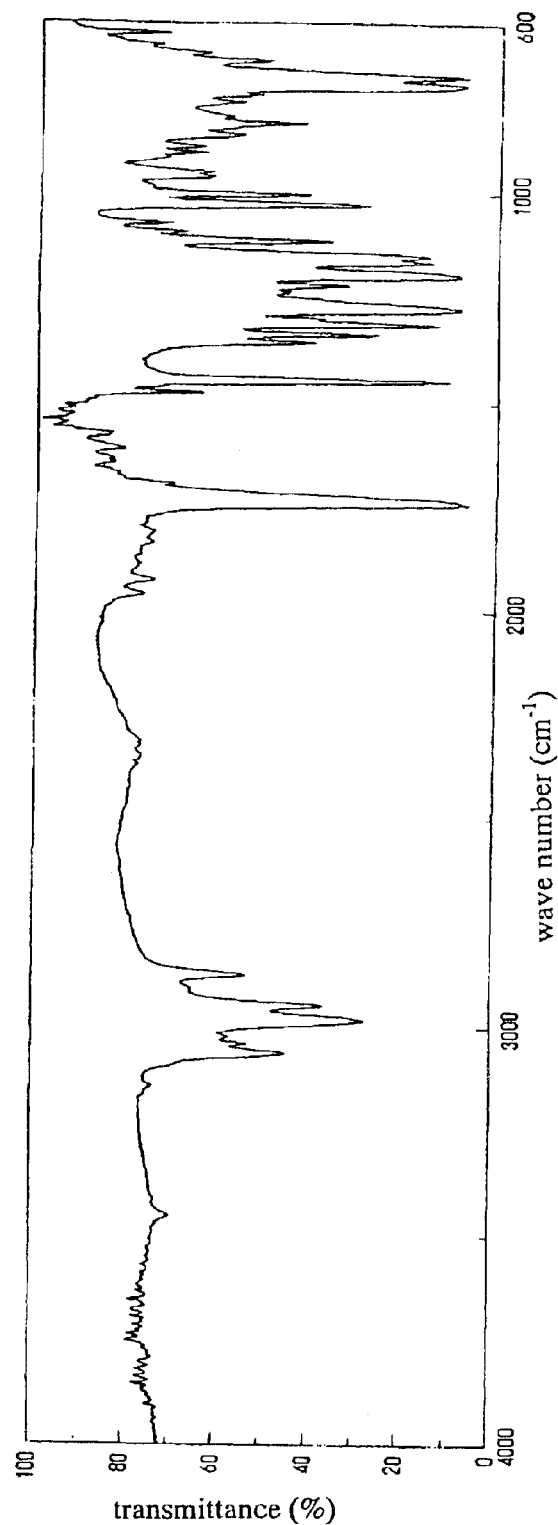
FIG. 10 is an infrared absorption (IR) spectrum of 5-(9-fluorenecarbonyloxy)bicyclo[2.2.1]hept-2-ene obtained in the example 5.

The ¹H-NMR spectrum and the infrared absorption (IR) spectrum of the product monomer are shown in FIG. 9 and FIG. 10.

Example 6

14 g of 5-(4-biphenylcarbonyloxy)bicyclo[2.2.1]hept-2-ene as the specified monomer, 0.2 g of 1-hexene as a molecular weight regulating agent, and 28 g of toluene were combined in a reaction vessel in which the air had been replaced with nitrogen gas, and were then heated to 80° C. To this reaction mixture was added 0.17 ml of a toluene solution of triethyl aluminum (0.6 mol/L) and 0.38 ml of a methanol modified WCl₆ toluene solution (0.025 mol/L), and a polymer was obtained by reaction for 3 hours at 80° C. A polymer with a weight average molecular weight (Mw) of 9.3×10⁴ and a molecular weight distribution (Mw/Mn)=2.32 was obtained.

The thus obtained polymer solution was placed in an autoclave, and a further 28 g of toluene was added. A hydrogenation catalyst RuHCl(CO)[P(C$_6$H$_5$)]$_3$ was added at a ratio of 500 ppm relative to the quantity of added monomer, and reaction was then conducted for 3 hours under a hydrogen gas pressure of 9 to 10 MPa and at a temperature of 160 to 165° C. Following completion of the reaction, the hydrogenated product [weight average molecular weight (Mw)=10.3×10$^4$, molecular weight distribution (Mw/Mn)=2.13, intrinsic viscosity ($\eta_{inh}$)=0.58, and glass transition temperature (Tg)=97.5° C.] was obtained by precipitation within a large volume of isopropanol. Determination of the hydrogenation ratio of the hydrogenated product using 400 MHz $^1$H-NMR measurements revealed that at least 99.0% of the olefin-based unsaturated bonds within the principal chain had been hydrogenated, whereas the side chain aromatic rings were essentially unhydrogenated. Furthermore, using this hydrogenated product, a disk was formed under the conditions described in the "Measurement of Retardation" section above, and measurement of the retardation revealed a maximum of 2 nm.

Figure 11:
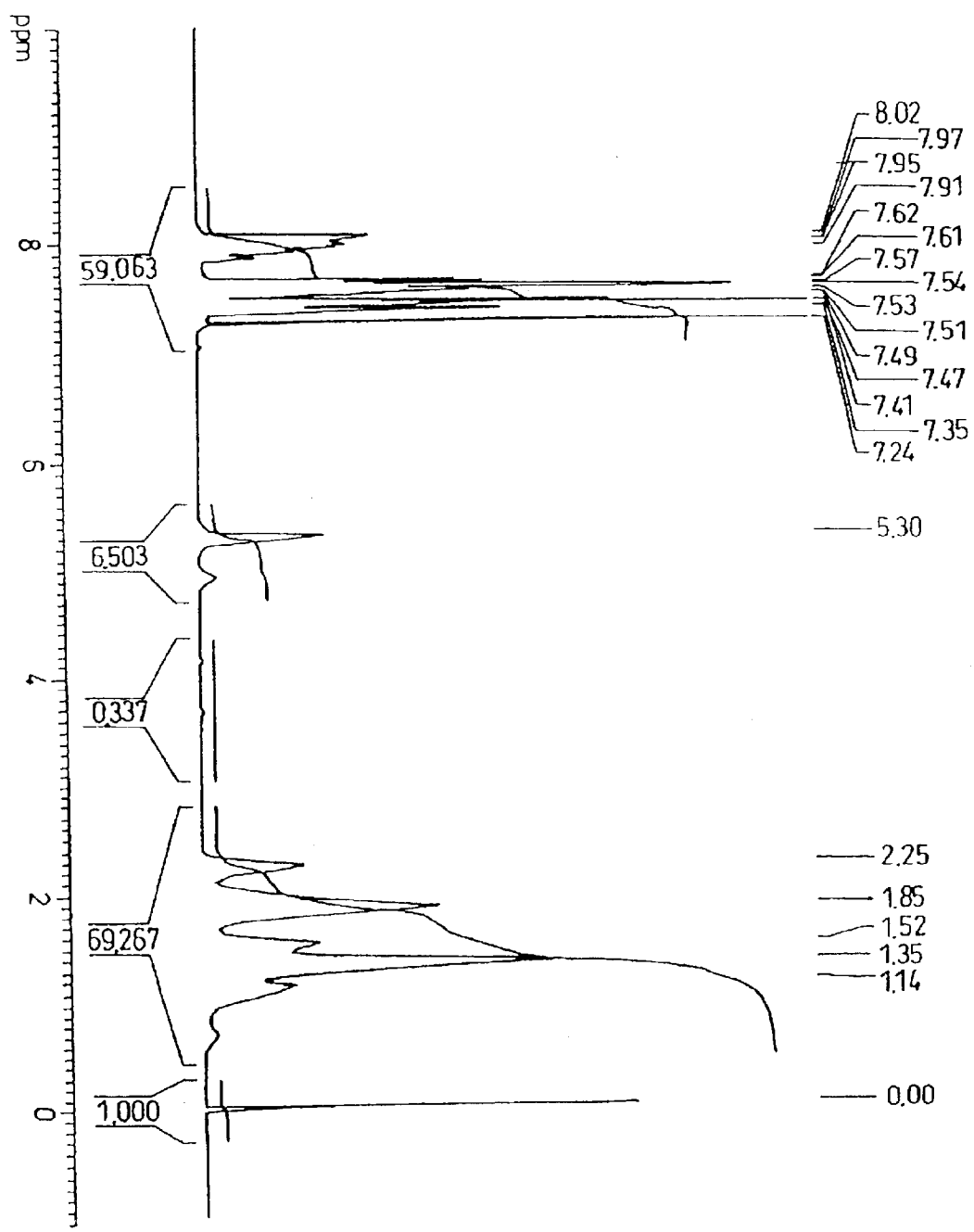
FIG. 11 is a $^1$H-NMR spectrum of a polymer obtained in an example 6.
Figure 12:
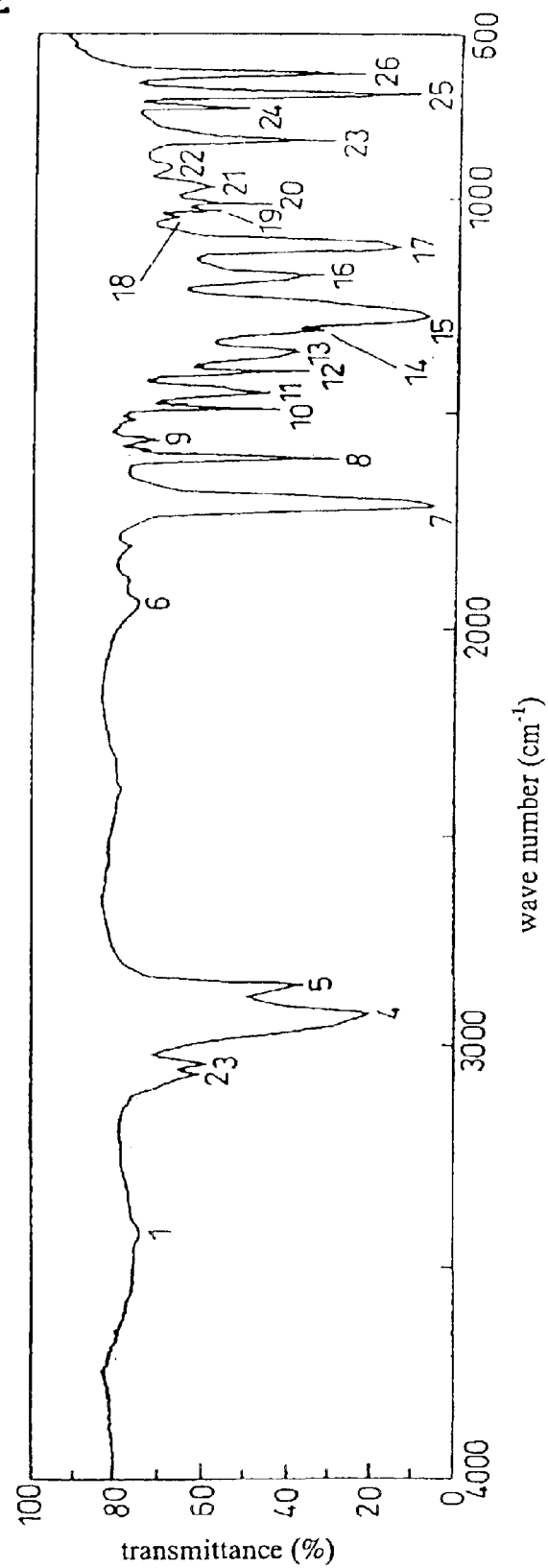
FIG. 12 is an infrared absorption (IR) spectrum of the polymer obtained in the example 6.

The $^1$H-NMR spectrum of the product polymer is shown in FIG. 11, and the infrared absorption (IR) spectrum is shown in FIG. 12.

Example 7

In a similar manner to the example 6, 14 g of 5-(1-naphthalenecarbonyloxy)bicyclo[2.2.1]hept-2-ene as the specified monomer, 0.2 g of 1-hexene as a molecular weight regulating agent, and 28 g of toluene were combined in a reaction vessel in which the air had been replaced with nitrogen gas, and were then heated to 80° C. To this reaction mixture was added 0.17 ml of a toluene solution of triethyl aluminum (0.6 mol/L) and 0.38 ml of a methanol modified WCl$_6$ toluene solution (0.025 mol/L), and a polymer was obtained by reaction for 3 hours at 80° C. A polymer with a weight average molecular weight (Mw) of 17.0×10$^4$ and Mw/Mn=4.00 was obtained. A hydrogenation reaction was also conducted in a similar manner to the example 6, and a corresponding hydrogenated product [weight average molecular weight (Mw)=16.1×10$^4$, molecular weight distribution (Mw/Mn)=3.20, intrinsic viscosity ($\eta_{inh}$)=0.74, and glass transition temperature (Tg)=74.0° C.] was obtained. Determination of the hydrogenation ratio of the hydrogenated product using 400 MHz $^1$H-NMR measurements revealed that at least 99.0% of the olefin-based unsaturated bonds within the principal chain had been hydrogenated, whereas the side chain aromatic rings were essentially unhydrogenated. Furthermore, using this hydrogenated product, a disk was formed under the conditions described in the "Measurement of Retardation" section above, and measurement of the retardation revealed a maximum of 9 nm.

Figure 13:
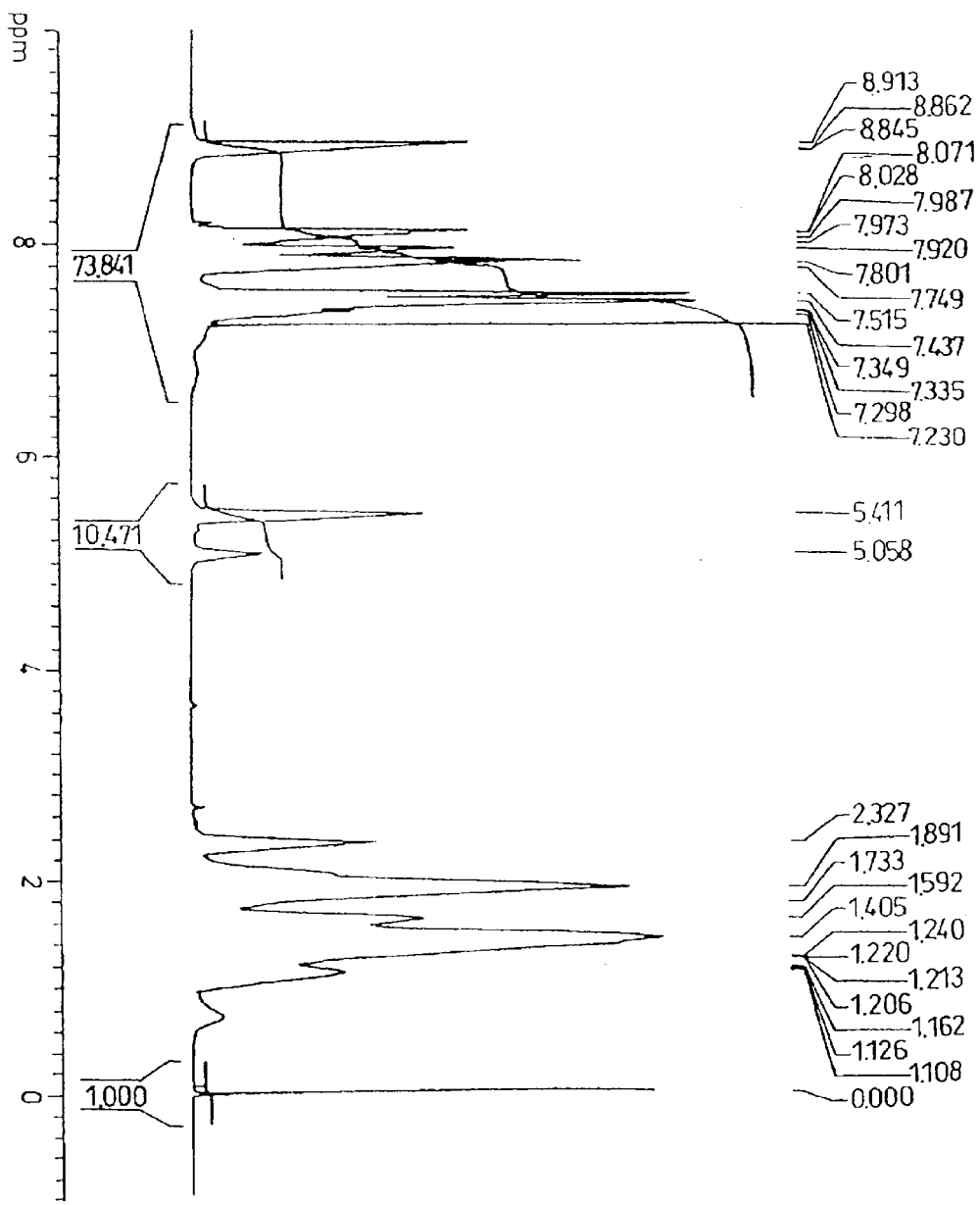
FIG. 13 is a $^1$H-NMR spectrum of a polymer obtained in an example 7.
Figure 14:
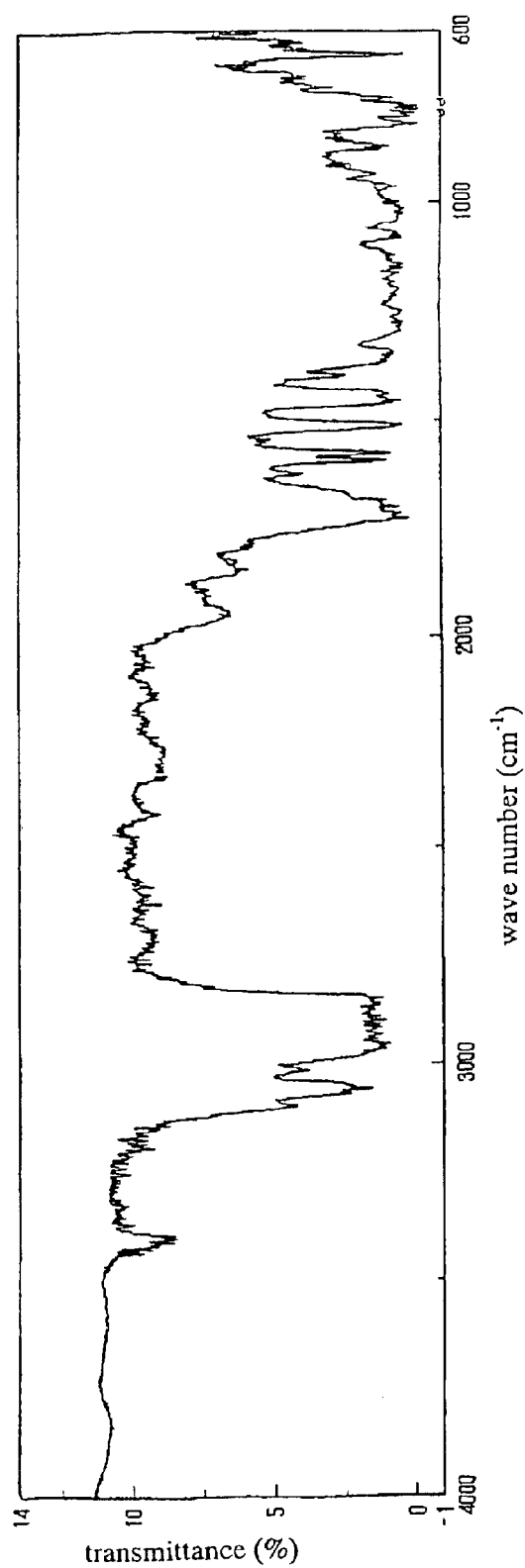
FIG. 14 is an infrared absorption (IR) spectrum of the polymer obtained in the example 7.

The $^1$H-NMR spectrum of the product polymer is shown in FIG. 13, and the infrared absorption (IR) spectrum is shown in FIG. 14.

Example 8

In a similar manner to the example 6, 14 g of 5-(2-naphthalenecarbonyloxy)bicyclo[2.2.1]hept-2-ene as the specified monomer, 0.2 g of 1-hexene as a molecular weight regulating agent, and 28 g of toluene were combined in a reaction vessel in which the air had been replaced with nitrogen gas, and were then heated to 80° C. To this reaction mixture was added 0.17 ml of a toluene solution of triethyl aluminum (0.6 mol/L) and 0.38 ml of a methanol modified WCl$_6$ toluene solution (0.025 mol/L), and a polymer was obtained by reaction for 3 hours at 80° C. A polymer with a weight average molecular weight (Mw) of 13.0×10$^4$ and a molecular weight distribution (Mw/Mn)=3.25 was obtained. A hydrogenation reaction was also conducted in a similar manner to the example 6, and a corresponding hydrogenated product [weight average molecular weight (Mw)=11.9×10$^4$, molecular weight distribution (Mw/Mn)=2.64, intrinsic viscosity ($\eta_{inh}$)=0.66, and glass transition temperature (Tg)= 82.4° C.] was obtained. Determination of the hydrogenation ratio of the hydrogenated product using 400 MHz $^1$H-NMR measurements revealed that at least 99.0% of the olefin-based unsaturated bonds within the principal chain had been hydrogenated, whereas the side chain aromatic rings were essentially unhydrogenated. Furthermore, using this hydrogenated product, a disk was formed under the conditions described in the "Measurement of Retardation" section above, and measurement of the retardation revealed a maximum of 3 nm.

Figure 15:
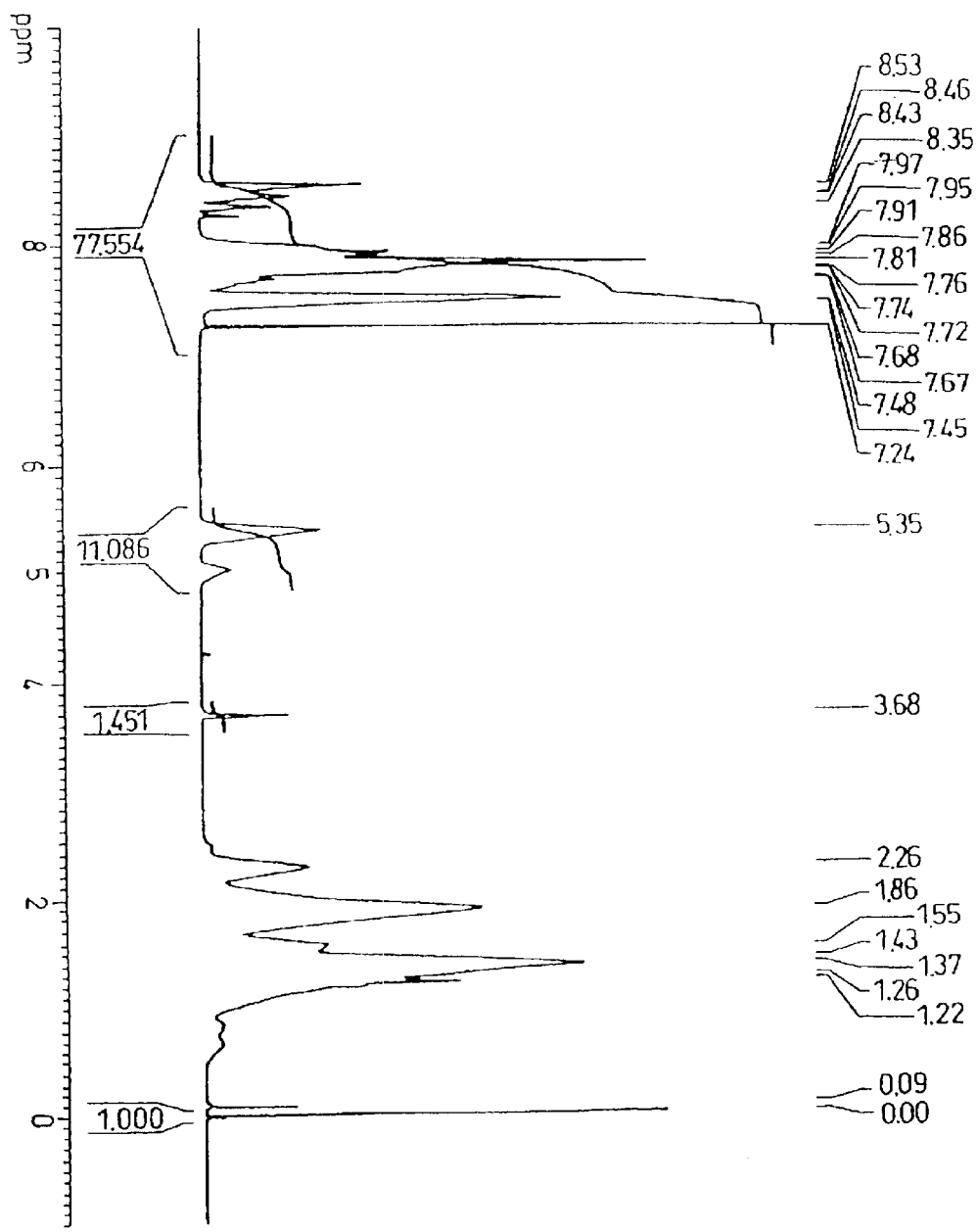
FIG. 15 is a $^1$H-NMR spectrum of a polymer obtained in an example 8.
Figure 16:
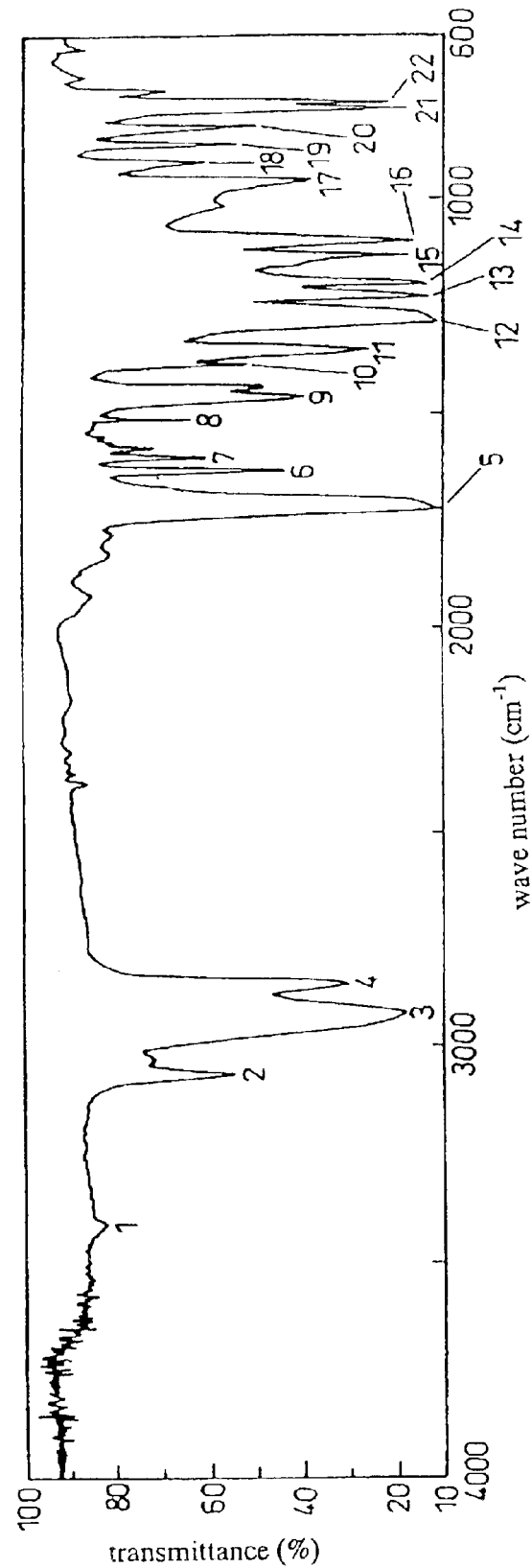
FIG. 16 is an infrared absorption (IR) spectrum of the polymer obtained in the example 8.

The $^1$H-NMR spectrum of the product polymer is shown in FIG. 15, and the infrared absorption (IR) spectrum is shown in FIG. 16.

Example 9

30 g of 5-(4-biphenylcarbonyloxy)bicyclo[2.2.1]hept-2-ene and 20 g of 8-methoxycarbonyl-8-methyltetracyclo [4.4.0.1$^{2,5}$.1$^{7,10}$]-3-dodecene of the formula shown below as the specified monomers,

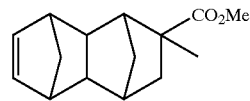

1.2 g of 1-hexene as a molecular weight regulating agent, and 100 g of toluene were combined in a reaction vessel in which the air had been replaced with nitrogen gas, and were then heated to 80° C. To this reaction mixture was added 0.5 ml of a toluene solution of triethyl aluminum (0.6 olefin) and 1.52 ml of a methanol modified WCl$_6$ toluene solution (0.025 mol/L), and a polymer was obtained by reaction for 3 hours at 80° C. A hydrogenation reaction was then conducted in a similar manner to the example 6, and a corresponding hydrogenated product [weight average molecular weight (Mw)=17.4×10$^4$, molecular weight distribution (Mw/Mn)=3.21, intrinsic viscosity ($\eta_{inh}$)=0.77, and glass transition temperature (Tg)=126° C.] was obtained. Determination of the hydrogenation ratio of the hydrogenated product using 400 MHz $^1$H-NMR measurements revealed that at least 99.0% of the olefin-based unsaturated bonds within the principal chain had been hydrogenated, whereas the side chain aromatic rings were essentially unhydrogenated. Furthermore, using this hydrogenated product, a disk was formed under the conditions described in the "Measurement of Retardation" section above, and measurement of the retardation revealed a maximum of 4 nm.

Figure 17:
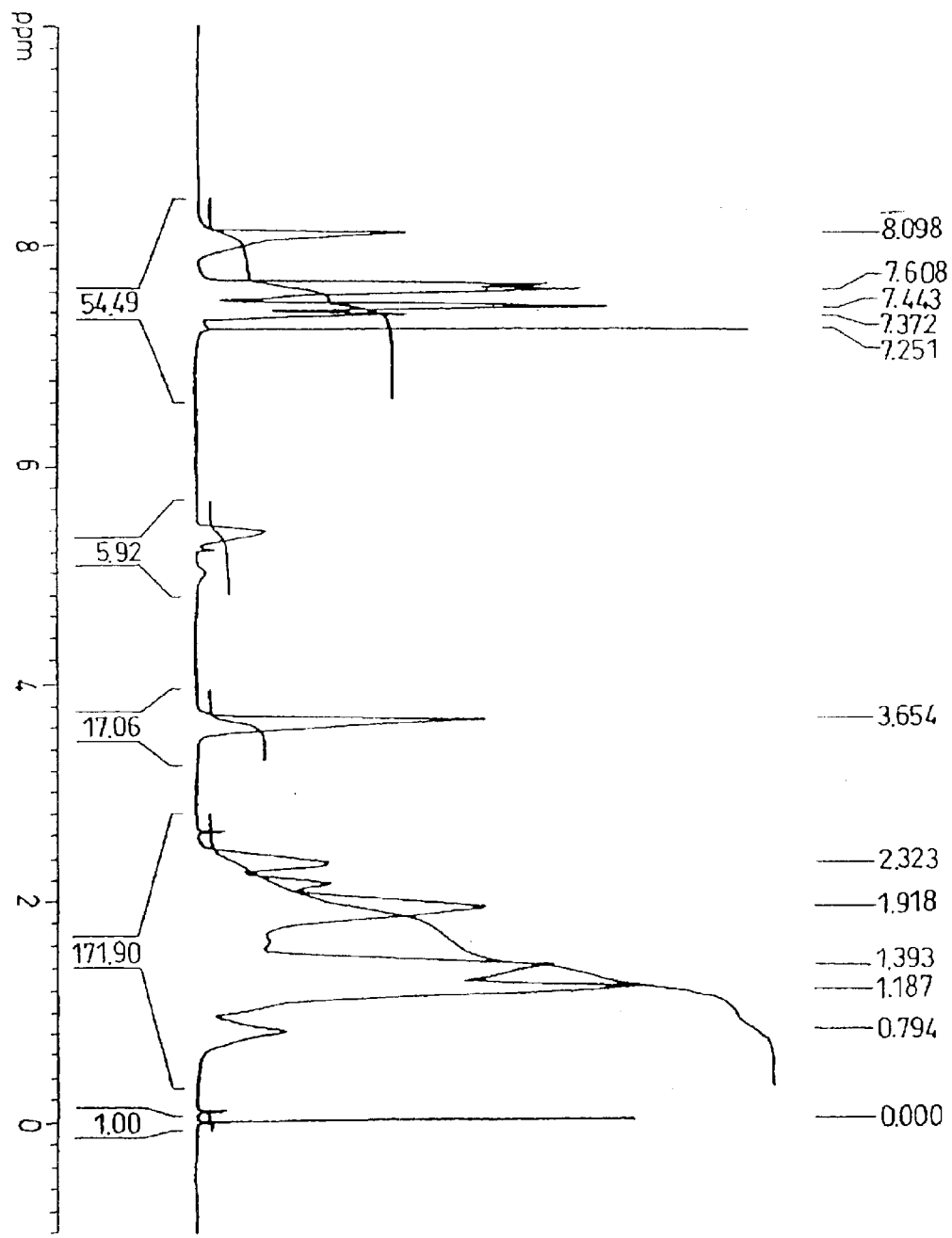
FIG. 17 is a $^1$H-NMR spectrum of a polymer obtained in an example 9.
Figure 18:
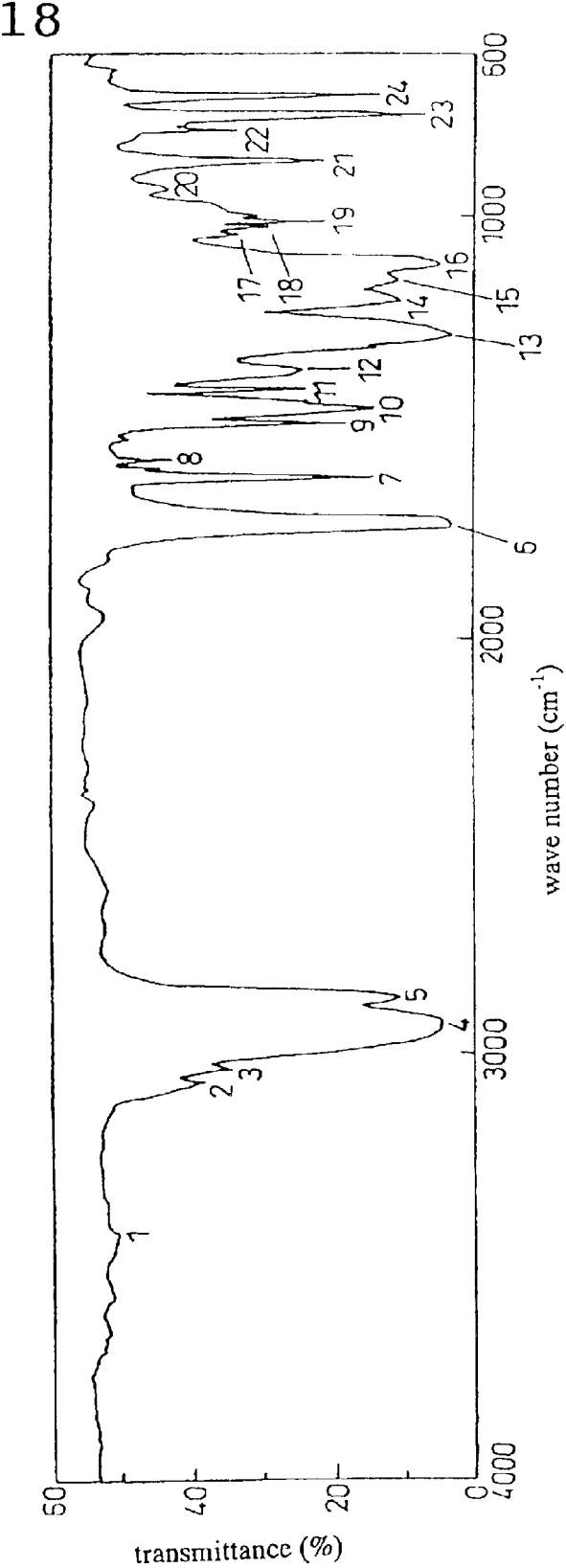
FIG. 18 is an infrared absorption (IR) spectrum of the polymer obtained in the example 9.

The $^1$H-NMR spectrum of the product polymer is shown in FIG. 17, and the infrared absorption (IR) spectrum is shown in FIG. 18.

Example 10

6.0 g of 5-(9-anthracenecarbonyloxy)bicyclo[2.2.1]hept-2-ene and 4.4 g of 8-methoxycarbonyl-8-methyltetracyclo [4.4.0.1$^{2,5}$.1$^{7,10}$]-3-dodecene as the specified monomers, 0.24 g of 1-hexene as a molecular weight regulating agent, and 21 g of toluene were combined in a reaction vessel in which the air had been replaced with nitrogen gas, and were then heated to 80° C. To this reaction mixture was added 0.1 ml of a toluene solution of triethyl aluminum (0.6 mol/L) and 0.31 ml of a methanol modified $WCl_6$ toluene solution (0.025 mol/L), and a polymer was obtained by reaction for 3 hours at 80° C. A hydrogenation reaction was then conducted in a similar manner to the example 6, and a corresponding hydrogenated product [glass transition temperature (Tg)=116° C.] was obtained. Determination of the hydrogenation ratio of the hydrogenated product using 400 MHz $^1$H-NMR measurements revealed that at least 99.0% of the olefin-based unsaturated bonds within the principal chain had been hydrogenated, whereas the side chain aromatic rings were essentially unhydrogenated. Furthermore, using this hydrogenated product, a disk was formed under the conditions described in the "Measurement of Retardation" section above, and measurement of the retardation revealed a maximum of 5 nm.

Figure 19:
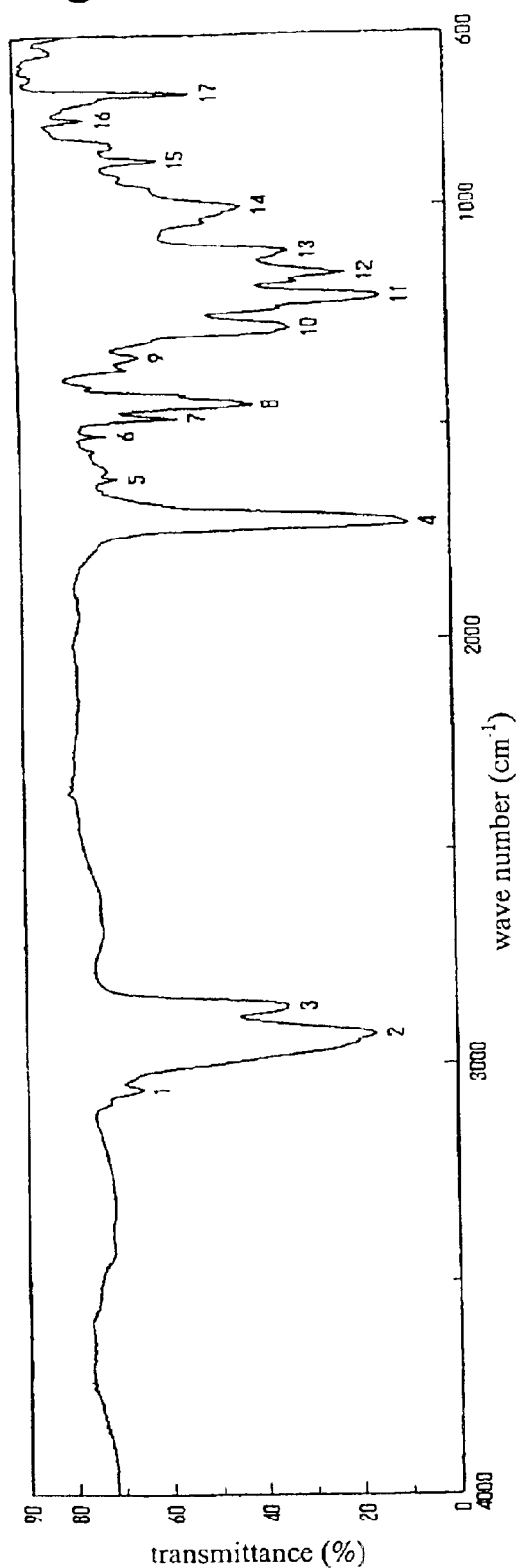
FIG. 19 is an infrared absorption (IR) spectrum of a polymer obtained in an example 10.

The infrared absorption (IR) spectrum of the product polymer is shown in FIG. 19.

Example 11

4.3 g of 5-(9-fluorenecarbonyloxy)bicyclo[2.2.1]hept-2-ene and 3.3 g of 8-methoxycarbonyl-8-methyltetracyclo[4.4.0.1$^{2,5}$.1$^{7,10}$]-3-dodecene as the specified monomers, 0.18 g of 1-hexene as a molecular weight regulating agent, and 15 g of toluene were combined in a reaction vessel in which the air had been replaced with nitrogen gas, and were then heated to 80° C. To this reaction mixture was added 0.07 ml of a toluene solution of triethyl aluminum (0.6 mol/L) and 0.23 ml of a methanol modified $WCl_6$ toluene solution (0.025 mol/L), and a polymer was obtained by reaction for 3 hours at 80° C. A hydrogenation reaction was then conducted in a similar manner to the example 6, and a corresponding hydrogenated product [glass transition temperature (Tg)=103° C.] was obtained. Determination of the hydrogenation ratio of the hydrogenated product using 400 MHz $^1$H-NMR measurements revealed that at least 99.0% of the olefin-based unsaturated bonds within the principal chain had been hydrogenated, whereas the side chain aromatic rings were essentially unhydrogenated. Furthermore, using this hydrogenated product, a disk was formed under the conditions described in the "Measurement of Retardation" section above, and measurement of the retardation revealed a maximum of 5 nm.

Figure 20:
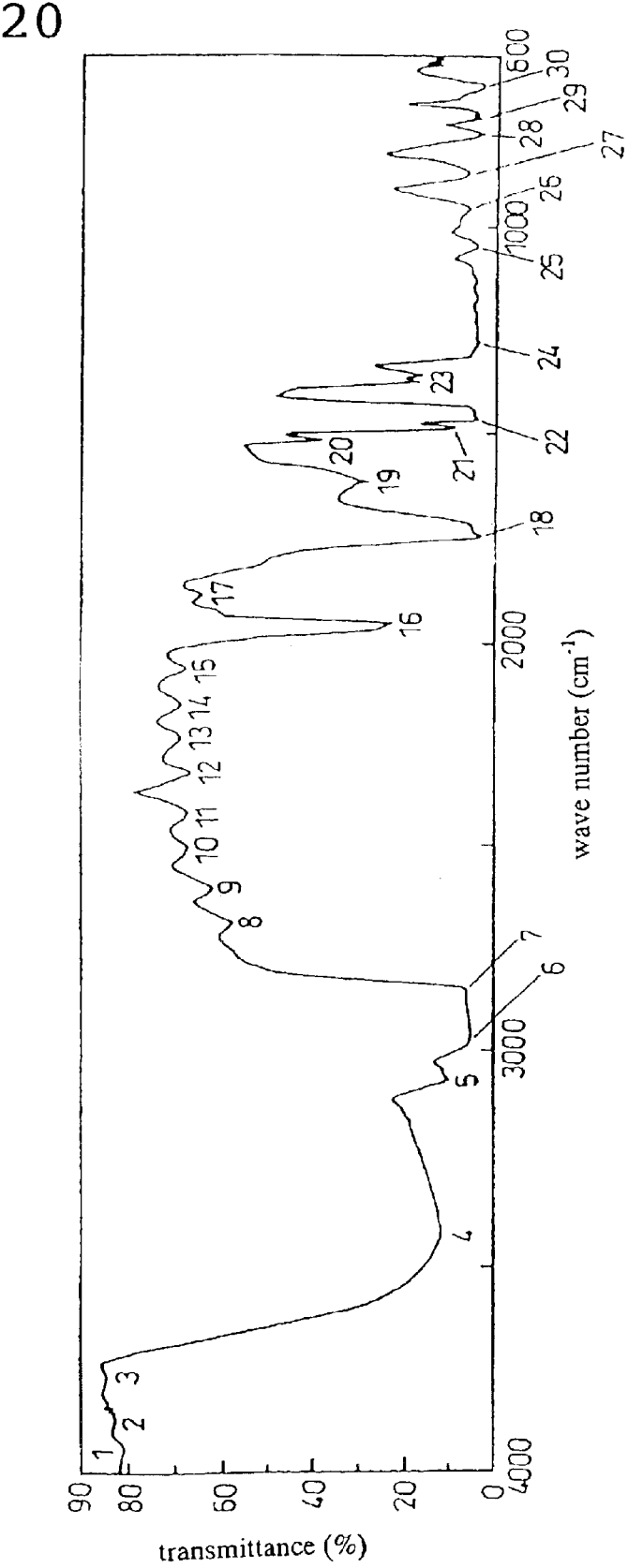
FIG. 20 is an infrared absorption (IR) spectrum of a polymer obtained in an example 11.

The infrared absorption (IR) spectrum of the product polymer is shown in FIG. 20.

Comparative Example 1

50 g of 8-methoxycarbonyl-8-methyltetracyclo[4.4.0.1$^{2,5}$.1$^{7,10}$]-3-dodecene as the specified monomer, 3.6 g of 1-hexene as a molecular weight regulating agent, and 100 g of toluene were combined in a reaction vessel in which the air had been replaced with nitrogen gas, and were then heated to 80° C. To this reaction mixture was added 0.09 ml of a toluene solution of triethyl aluminum (0.6 mol/L) and 0.29 ml of a methanol modified $WCl_6$ toluene solution (0.025 mol/L), and a polymer was obtained by reaction for 3 hours at 80° C. A hydrogenation reaction was then conducted in a similar manner to the example 6, and a corresponding hydrogenated product [glass transition temperature Tg)=164° C., weight average molecular weight (Mw)=56,000, molecular weight distribution (Mw/Mn)=3.2] was obtained. Determination of the hydrogenation ratio of the hydrogenated product using 400 MHz $^1$H-NMR measurements revealed that at least 99.0% of the olefin-based unsaturated bonds within the principal chain had been hydrogenated. Furthermore, using this hydrogenated product, a disk was formed under the conditions described in the "Measurement of Retardation" section above, and measurement of the retardation revealed a maximum of 20 nm.

The results of the retardation measurements for the examples 6 to 11 and the comparative example 1, and the glass transition temperatures for the hydrogenated products, are shown in Table 1.

TABLE 1

| Example | Retardation value (nm) | Glass transition temperature (° C.) |
| --- | --- | --- |
| Example 6 | 2 | 97.5 |
| Example 7 | 9 | 74.0 |
| Example 8 | 3 | 82.4 |
| Example 9 | 4 | 126.0 |
| Example 10 | 5 | 116.0 |
| Example 11 | 5 | 103.0 |
| Comparative Example 1 | 20 | 167.0 |

Industrial Applicability

A polymer and a hydrogenated product thereof produced from a norbornene derivative of the present invention retain excellent transparency and heat resistance, and a low level of water absorption, while displaying a lower birefringence than conventional cyclic olefin resins. Accordingly, the norbornene derivatives of the present invention are extremely useful optical resin precursor monomers. Because polymers and hydrogenated products thereof according to the present invention retain excellent transparency, heat resistance, and water resistance, while displaying a low birefringence, they can be applied to optical materials which require extremely precise optical design such as optical disks, magneto-optical disks, optical lenses (such as Fθ lenses, pickup lenses, laser printer lenses and camera lenses), spectacle lenses, optical films or sheets (such as display films, retardation films, polarizing films, polarizing plate protective films, diffusion films, antireflective films, liquid crystal substrates, EL substrates, electronic paper substrates, touch panel substrates and PDP front plates), transparent conductive film substrates, optical fibers, light guide plates, optical cards, optical mirrors, IC, LSI and LED sealing materials.

What is claimed is:

1. A norbornene derivative represented by a general formula (1m) shown below:

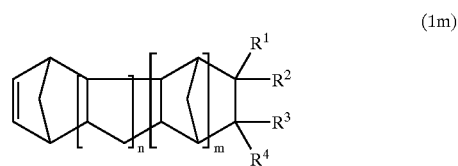

(1m)

wherein, at least one of $R^1$ to $R^4$ is a group selected from the group consisting of an aromatic ring-containing group represented by a general formula (1-1) shown below and an aromatic ring-containing group represented by a general formula (1-2) shown below, any remaining groups among $R^1$, $R^2$, $R^3$ and $R^4$, where present, represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, and m and n each represent, independently, an integer from 0 to 2;

(1-1)

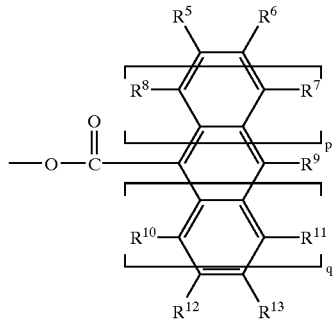

wherein, $R^5$ to $R^{13}$ each represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, and p and q each represent, independently an integer from 0 to 2, provided that in a case in which p=q=0, $R^6$ and $R^9$, and/or $R^{13}$ and $R^9$, are bonded to each other to form a carbon homocyclic ring or a heterocyclic ring, said carbon homocyclic ring or heterocyclic ring being a single ring structure, or forming a polycyclic structure by condensation with at least one other ring, or alternatively at least one of $R^5$, $R^6$, $R^9$, $R^{12}$ and $R^{13}$ is a substituted or unsubstituted aromatic group;

(1-2)

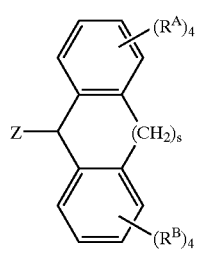

[wherein, Z, $R^A$ and $R^B$ each represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, provided that one of $R^A$, $R^B$ and Z is a group represented by a formula —C(O)O— in which the carbonyl group side is bonded to a carbon atom of a ring structure within said formula (1-2), and s represents an integer of 0 or greater].

2. The norbornene derivative according to claim 1, wherein in said general formula (1m), n is 0, and m is either 0 or 1.

3. The norbornene derivative according to claim 1, wherein in said general formula (1-1), p is either 0 or 1, and q is either 0 or 1, and in said general formula (1-2), s is either 0 or 1.

4. The norbornene derivative according to claim 2, comprising at least 10 mol % of stereoisomers in which at least one of said groups selected from the group consisting of groups represented by said general formula (1-1) and groups represented by said general formula (1-2) is bonded to an at position shown in a partial structural formula represented by a formula (3) shown below:

(3)

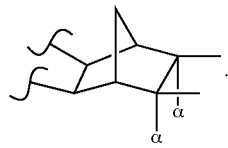

5. A norbornene-based ring opening polymer comprising a structural unit (1) represented by a general formula (1) shown below:

(1)

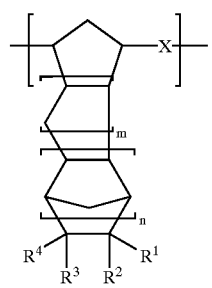

[wherein, X is a group represented by a formula —CH═CH— or a group represented by a formula —CH$_2$—CH$_2$—, and m, n, $R^1$, $R^2$, $R^3$ and $R^4$ are as defined above in relation to said general formula (1m) in claim 1], wherein a plurality of X groups which exist may be either identical or different.

6. The norbornene-based ring opening polymer according to claim 5, further comprising a structural unit (2) represented by a general formula (2) shown below:

(2)

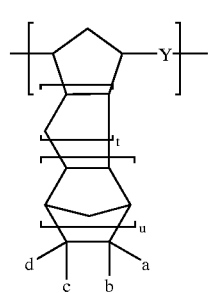

[wherein, t and u each represent, independently, an integer from 0 to 2, Y is a group represented by a formula —CH═CH— or a group represented by a formula —CH$_2$—CH$_2$—, a, b, c and d each represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, or alternatively a and b, b and c, or c and d may be bonded to each other to form a carbon homocyclic ring or a heterocyclic ring (and said carbon homocyclic ring or heterocyclic ring may be a single ring structure, or may form a polycyclic structure by condensation with another ring)], wherein a plurality of Y groups which exist may be either identical or different.

7. The norbornene-based ring opening polymer according to claim 6, wherein a proportion of said structural unit (2) relative to a combined total of said structural unit (1) and said structural unit (2) is no more than 95% by weight.

8. A method of producing a norbornene-based ring opening polymer with a structural unit (1) represented by said general formula (1) in claim 5 in which X is a group represented by a formula —CH=CH—, wherein a norbornene-based monomer comprising a norbornene derivative represented by a general formula (1m) shown below is subjected to ring opening polymerization:

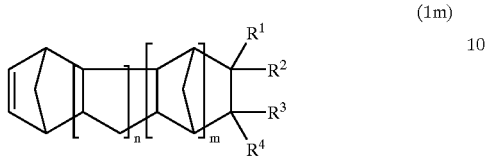

(1m)

[wherein, m, n, $R^1$, $R^2$, $R^3$ and $R^4$ are as defined above in relation to said general formula (1m) in claim 1].

9. The method of producing a norbornene-based ring opening polymer according to claim 8, wherein said norbornene-based monomer comprises a norbornene-based monomer represented by a general formula (2m) shown below in addition to said norbornene derivative represented by said general formula (1m), and said norbornene-based ring opening polymer comprises a structural unit (1) represented by said general formula (1) in which X is a group represented by a formula —CH=CH—, and a structural unit (2) represented by said general formula (2) in claim 6 in which Y is a group represented by a formula —CH=CH—:

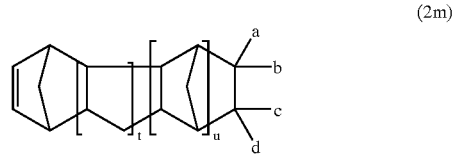

(2m)

wherein, t and u each represent, independently, an integer from 0 to 2; a, b, c and d each represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, or alternatively a and b, b and c, or c and d may be bonded to each other to form a carbon homocyclic ring or a heterocyclic ring, and said carbon homocyclic ring or heterocyclic ring may be a single ring structure, or may form a polycyclic structure by condensation with another ring.

10. A method of producing a norbornene-based ring opening polymer with a structural unit (1) represented by said general formula (1) according to claim 5 (in which X is a group represented by a formula —CH$_2$—CH$_2$—), wherein a norbornene-based monomer comprising a norbornene derivative represented by a general formula (1m) shown below is subjected to ring opening polymerization:

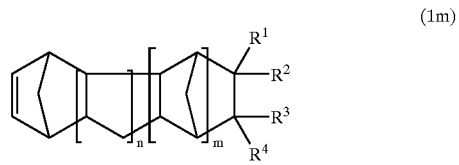

(1m)

[wherein, m, n, $R^1$, $R^2$, $R^3$ and $R^4$ are as defined above in relation to said general formula (1m) according to claim 1].

11. The method of producing a norbornene-based ring opening polymer according to claim 10, wherein said norbornene-based monomer comprises a norbornene-based monomer represented by a general formula (2m) shown below in addition to said norbornene derivative represented by said general formula (1m), and said norbornene-based ring opening polymer comprises a structural unit (1) represented by said general formula (1) (in which X is a group represented by a formula —CH$_2$—CH$_2$—), and a structural unit (2) represented by said general formula (2) according to claim 6 (in which Y is a group represented by a formula —CH$_2$—CH$_2$—):

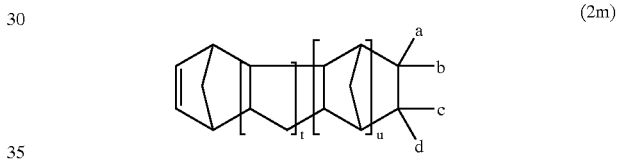

(2m)

t and u each represent, independently, an integer from 0 to 2; a, b, c and d each represent, independently, a hydrogen atom; a halogen atom; a substituted or unsubstituted monovalent hydrocarbon group of 1 to 30 carbon atoms which may contain a linkage group containing oxygen, nitrogen, sulfur or silicon; or a monovalent polar group, or alternatively a and b, b and c, or c and d may be bonded to each other to form a carbon homocyclic ring or a heterocyclic ring, and said carbon homocyclic ring or heterocyclic ring may be a single ring structure, or may form a polycyclic structure by condensation with another ring.

wherein, t, u, a, b, c and d are as defined above in relation to said general formula (2) according to claim 6].

* * * * *